(12) United States Patent
Tsujita

(10) Patent No.: US 8,948,485 B2
(45) Date of Patent: Feb. 3, 2015

(54) ULTRASONIC DIAGNOSTIC APPARATUS, ULTRASONIC IMAGE PROCESSING APPARATUS, ULTRASONIC IMAGE PROCESSING PROGRAM, AND ULTRASONIC IMAGE GENERATION METHOD

(75) Inventor: Takehiro Tsujita, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 503 days.

(21) Appl. No.: 13/377,384

(22) PCT Filed: Jun. 4, 2010

(86) PCT No.: PCT/JP2010/059502
§ 371 (c)(1),
(2), (4) Date: Dec. 9, 2011

(87) PCT Pub. No.: WO2010/143587
PCT Pub. Date: Dec. 16, 2010

(65) Prior Publication Data
US 2012/0087564 A1   Apr. 12, 2012

(30) Foreign Application Priority Data
Jun. 10, 2009   (JP) ................................. 2009-139101

(51) Int. Cl.
*G06K 9/00* (2006.01)
*A61B 8/08* (2006.01)
*G01S 15/89* (2006.01)

(52) U.S. Cl.
CPC ............... *A61B 8/0808* (2013.01); *A61B 8/483* (2013.01); *A61B 8/5223* (2013.01); *G01S 15/8993* (2013.01)
USPC ............................ 382/131; 382/128; 382/132

(58) Field of Classification Search
USPC .......................................................... 382/131
See application file for complete search history.

(56) References Cited

U.S. PATENT DOCUMENTS 6,480,732 B1 * 11/2002 Tanaka et al. .................. 600/425
7,630,533 B2 * 12/2009 Ruth et al. ..................... 382/131
(Continued)

FOREIGN PATENT DOCUMENTS

EP       1938754 A1 *  7/2008  ............... A61B 8/08
EP       2441389 A1 *  4/2012
(Continued)

OTHER PUBLICATIONS

English Translation of JP2008-259605, Tsujita, Takeyoshi, "Ultrasonic Diagnostic Equipment", Oct. 30, 2008, p. 1-17.*
International Search Report from International Application No. PCT/JP2010/059502 mailed Aug. 17, 2010.

*Primary Examiner* — Gandhi Thirugnanam
(74) *Attorney, Agent, or Firm* — Brundidge & Stanger, P.C.

(57) ABSTRACT

In order to generate a three-dimensional tomographic image in which the visibility of specific tissue that an examiner wants is enhanced, an ultrasonic diagnostic apparatus 100 of the present invention includes: an offset calculating section 16 which increases or decreases the brightness value of each voxel according to the brightness value of each voxel of a three-dimensional tomographic image volume data. The amount of increase or decrease in the brightness value of each voxel of the offset calculating section is adjustable through a control panel 26, and a tomographic image volume rendering section generates the three-dimensional tomographic image on the basis of a three-dimensional tomographic image volume data in which the brightness value is offset by the offset calculating section.

13 Claims, 27 Drawing Sheets

(56) References Cited

U.S. PATENT DOCUMENTS

| | | | |
|---|---|---|---|
| 8,047,992 B2* | 11/2011 | Hashimoto et al. | 600/443 |
| 2005/0207630 A1* | 9/2005 | Chan et al. | 382/131 |
| 2006/0229513 A1* | 10/2006 | Wakai | 600/407 |
| 2011/0026800 A1* | 2/2011 | Tonomura et al. | 382/131 |
| 2011/0218440 A1* | 9/2011 | Fujii et al. | 600/443 |
| 2011/0224549 A1* | 9/2011 | Tsujita | 600/443 |
| 2012/0087564 A1* | 4/2012 | Tsujita | 382/131 |

FOREIGN PATENT DOCUMENTS

| | | |
|---|---|---|
| JP | 2003061964 | 3/2003 |
| JP | 2006-288495 | 10/2006 |
| JP | 2007-54504 | 3/2007 |
| JP | 2008142327 | 6/2008 |
| JP | 2008-200441 | 9/2008 |
| JP | 2008-259605 | 10/2008 |
| WO | 2006121031 | 11/2006 |
| WO | 2007046272 | 4/2007 |

* cited by examiner

ULTRASONIC DIAGNOSTIC APPARATUS, ULTRASONIC IMAGE PROCESSING APPARATUS, ULTRASONIC IMAGE PROCESSING PROGRAM, AND ULTRASONIC IMAGE GENERATION METHOD

TECHNICAL FIELD

The present invention relates to an ultrasonic diagnostic apparatus, an ultrasonic image processing apparatus, an ultrasonic image processing program, and an ultrasonic image generation method and in particular, to a technique of generating a two-dimensional projection image (three-dimensional tomographic image) on the basis of three-dimensional tomographic image volume data obtained from reflected echo signals of plural tomographic planes of an object.

BACKGROUND ART

The ultrasonic diagnostic apparatus transmits an ultrasonic wave into the inside of the object by an ultrasonic probe including plural ultrasonic transducers, receives a reflected echo signal of the ultrasonic wave corresponding to the structure of body tissue from the inside of the object, generates a tomographic image, for example, a B-mode image on the basis of the reflected echo signal, and displays the B-mode image for diagnosis.

In such an ultrasonic diagnostic apparatus, generating three-dimensional tomographic image volume data from reflected echo signals of plural tomographic planes of the object measured by ultrasonic scanning in a short-axis direction of the ultrasonic probe and generating an image (three-dimensional tomographic image) by projecting the three-dimensional tomographic image volume data onto the two-dimensional projection plane using a volume rendering technique are known.

The volume rendering technique is to generate a three-dimensional tomographic image by performing cumulative addition of the brightness values of plural voxels, which are arrayed in the line-of-sight direction when the three-dimensional tomographic image volume data is viewed from a point on the two-dimensional projection plane, along the line-of-sight direction and setting the result as a pixel value (brightness) of the two-dimensional projection plane while correcting the brightness values by transparency/opacity of each voxel, for example.

On the other hand, the brightness of each voxel obtained by ultrasonic scanning is determined according to the acoustic impedance of tissue in the object, ultrasonic attenuation due to propagation in the object, and the like. For this reason, it is difficult to generate a three-dimensional tomographic image which characterizes only specific tissues to be diagnosed (for example, with enhanced brightness).

In order to cope with such a problem, for example, a maximum value projection method of displaying only high-brightness tissue of the three-dimensional tomographic image volume data or a minimum value projection method of displaying only low-brightness tissue is generally used. In addition, as disclosed in PTL 1, reversing the brightness level of a B-mode image so that the three-dimensional structure of a low echo region can be easily viewed is known.

CITATION LIST

Patent Literature

[PTL 1] JP-A-2008-200441

SUMMARY OF INVENTION

Technical Problem

In the conventional technique disclosed in the above Patent Literature and the like, generating a three-dimensional tomographic image in which the visibility of specific tissue that the examiner wants (for example, tissue to be diagnosed) is enhanced is not considered.

That is, since the applications of each one of the maximum value projection method, the minimum value projection method, and the method of reversing the brightness level of a B-mode image are limited, a three-dimensional tomographic image in which the visibility of specific tissue that the examiner wants is enhanced cannot always be freely generated. For example, such methods can generate a three-dimensional tomographic image in which the visibility of high-brightness tissue or low-brightness tissue is enhanced, but it is difficult to generate a three-dimensional tomographic image in which the visibility of tissue with medium brightness thereof is enhanced.

Therefore, it is an objective of the present invention to generate a three-dimensional tomographic image in which the visibility of specific tissue that the examiner wants is enhanced.

Solution to Problem

An ultrasonic diagnostic apparatus of the present invention includes: an ultrasonic probe which transmits or receives an ultrasonic wave to or from an object; a tomographic image volume data generating section which generates three-dimensional tomographic image volume data on the basis of reflected echo signals of plural tomographic planes of the object measured by the ultrasonic probe; a tomographic image volume rendering section which generates a three-dimensional tomographic image seen from at least one line-of-sight direction on a two-dimensional projection plane on the basis of the three-dimensional tomographic image volume data; a display section which displays the three-dimensional tomographic image; and an offset calculating section which increases or decreases the brightness value of each voxel according to the brightness value of each voxel of the three-dimensional tomographic image volume data, and is characterized in that the amount of increase or decrease in the brightness value of each voxel of the offset calculating section is adjustable through an input interface and the tomographic image volume rendering section generates the three-dimensional tomographic image on the basis of the three-dimensional tomographic image volume data in which the brightness value is offset by the offset calculating section.

According to this, since an examiner can adjust the amount of increase or decrease in the brightness value of each voxel of the offset calculating section through the input interface, it is possible to generate a three-dimensional tomographic image in which only tissue with a specific brightness value is emphasized. Therefore, it is possible to generate a three-dimensional tomographic image with enhanced visibility of desired specific tissue by adjusting the amount of increase in the brightness value of the desired specific tissue, adjusting the amount of decrease in the brightness value of tissue other than the desired specific tissue, or adjusting both of them. For example, if the examiner knows the brightness value of desired specific tissue, it is possible to enlarge the amount of increase (offset amount) in the brightness value corresponding to the vicinity of the brightness value in advance. Moreover, for example, in the case where it is difficult to see desired specific tissue since it is hidden behind high-brightness tissue when viewing the generated three-dimensional tomographic image, it becomes difficult for the high-brightness tissue as a wall to be reflected on the three-dimensional tomographic image if the amount of decrease (offset amount) in the brightness value corresponding to the vicinity of the high brightness value is set to be large. As a result, it is possible to improve the visibility of the desired specific tissue.

In addition, when an elastic image volume data generating section which generates three-dimensional elastic image volume data on the basis of the reflected echo signals of the plural tomographic planes of the object is provided, the offset calculating section may be configured to increase or decrease the brightness value of each corresponding voxel of the three-dimensional tomographic image volume data according to the value of elasticity of each voxel of the three-dimensional elastic image volume data.

According to this, the examiner can generate a three-dimensional tomographic image with enhanced visibility of tissue, which has a specific value of elasticity, on the basis of the value of elasticity (stiffness or softness of tissue) of desired specific tissue. For example, if the examiner knows the value of elasticity of desired specific tissue, it is possible to enlarge the amount of increase (offset amount) in the brightness value corresponding to the vicinity of the value of elasticity in advance. On the other hand, when the examiner wants to observe hard (or soft) tissue, it is possible to find and observe the hard (or soft) tissue if the amount of increase (offset amount) in the brightness value corresponding to the high (or low) value of elasticity is set high.

In addition, the offset calculating section may have plural offset tables in which boundary values for dividing a range of the brightness value of each voxel of the three-dimensional tomographic image volume data or a range of the value of elasticity of each voxel of the three-dimensional elastic image volume data into plural regions and the amount of increase or decrease in the brightness value in each of the plural divided regions are set, and the brightness value of each voxel of the three-dimensional tomographic image volume data may be increased or decreased on the basis of the offset table selected from the plural offset tables through the input interface.

For example, plural offset tables, such as an offset table for enhancing the visibility of tissue with low brightness value, an offset table for enhancing the visibility of tissue with intermediate brightness value, and an offset table for enhancing the visibility of tissue with high brightness value, may be prepared as default. In this case, since the examiner only needs to select one of the offset tables, it is good in terms of usability. In addition, since the boundary value and the amount of increase or decrease of the offset table can be adjusted through the input interface, finer adjustment can be performed. As a result, it is possible to further improve the visibility of tissue that the examiner wants.

In addition, the tomographic image volume rendering section may have an opacity table in which transparency/opacity is set according to the brightness value of each voxel of the three-dimensional tomographic image volume data, and the three-dimensional tomographic image may be generated on the basis of the brightness value of each voxel on a line of sight in the at least one line-of-sight direction of the three-dimensional tomographic image volume data and the transparency/opacity based on the opacity table.

In addition, the tomographic image volume rendering section may have a brightness-opacity map in which transparency/opacity and a color code are set according to the brightness value of each voxel of the three-dimensional tomographic image volume data. A two-dimensional tomographic image may be generated by converting a color of each voxel of tomographic image data of at least one section of the three-dimensional tomographic image volume data, in which the brightness value is offset, on the basis of the brightness-opacity map, and the display section may display the three-dimensional tomographic image, the two-dimensional tomographic image, and the brightness-opacity map.

That is, the transparency/opacity of each voxel becomes an index indicating how much the voxel is reflected on the three-dimensional tomographic image. Therefore, by performing color display according to the transparency/opacity of each voxel of the two-dimensional tomographic image, the examiner can recognize which part of the two-dimensional tomographic image and how much is reflected on the three-dimensional tomographic image by referring to the two-dimensional tomographic image. In addition, by referring to the two-dimensional tomographic image, it becomes easy to perform adjustment of an offset table for improving the visibility of desired specific tissue. Regarding color encoding on a two-dimensional tomographic image based on the transparency/opacity, when an examiner changes (adjusts) the offset amount, the position of the brightness boundary, or the gain adjustment value of the tomographic image input value or the opacity table through the control panel, that is, when the examiner performs an operation of causing a change in opacity processing on the three-dimensional tomographic image, encoding processing is performed for a fixed time (for example, about 1 to 5 seconds) so that the examiner can see the influence of the operation on the three-dimensional tomographic image through the tomographic image. After the elapse of the fixed time (for example, about 1 to 5 seconds), it is possible to end the transparency/opacity color encoding and to display a normal tomographic image so that normal diagnosis can be smoothly performed.

Advantageous Effects of Invention

According to the present invention, it is possible to generate a three-dimensional tomographic image in which the visibility of specific tissue that an examiner wants is enhanced.

DESCRIPTION OF EMBODIMENTS

Hereinafter, embodiments of an ultrasonic diagnostic apparatus, an ultrasonic image processing apparatus, an ultrasonic image processing program, and an ultrasonic image generation method to which the present invention is applied will be described.

(First Embodiment)

Figure 1:
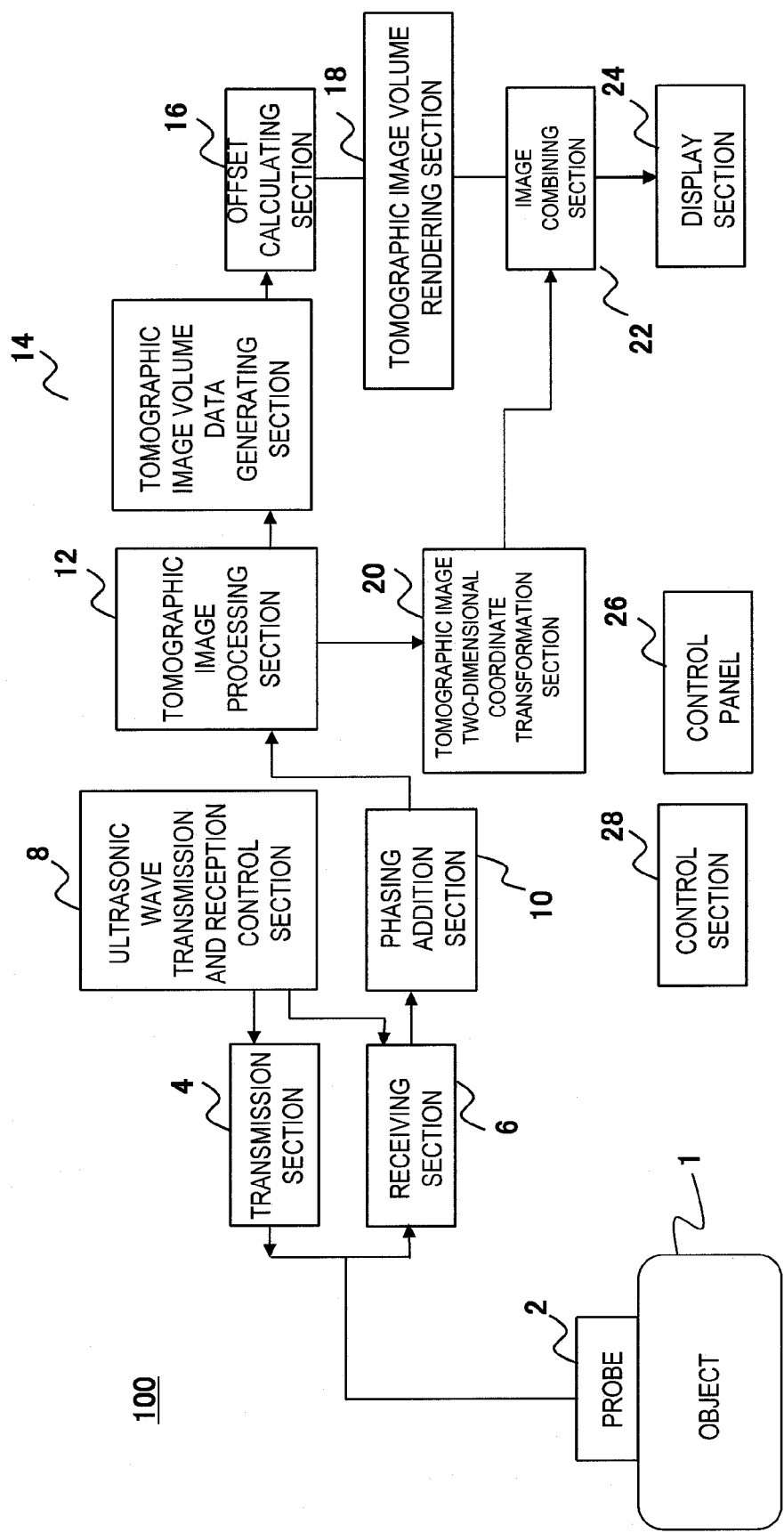
FIG. 1 is a block diagram showing the entire configuration of an ultrasonic diagnostic apparatus of a first embodiment.

A first embodiment of an ultrasonic diagnostic apparatus to which the present invention is applied will be described with reference to the drawings. FIG. 1 is a block diagram showing the entire configuration of an ultrasonic diagnostic apparatus of a first embodiment.

As shown in FIG. 1, an ultrasonic diagnostic apparatus 100 of the present embodiment is configured to include: an ultrasonic probe 2 which transmits or receives an ultrasonic wave to or from an object 1; a transmission section 4 which supplies a driving signal to the ultrasonic probe 2; a receiving section 6 which receives a reflected echo signal received by the ultrasonic probe 2; an ultrasonic wave transmission and reception control section 8 which controls transmission and reception of the transmission section 4 and the receiving section 6; and a phasing addition section 10 which generates an RF signal by phase addition of the reflected echo signal received by the receiving section 6.

In addition, the ultrasonic diagnostic apparatus 100 includes: a tomographic image processing section 12 which generates tomographic image data by performing various kinds of processing, such as logarithmic compression, filtering, and image processing, on an RF signal (ultrasonic signal) output from the phasing addition section 10; a tomographic image volume data generating section 14 which generates three-dimensional tomographic image volume data perpendicular to each axis by performing coordinate transformation for the tomographic image data of plural tomographic planes of the object 1; an offset calculating section 16 which is a characteristic section of the present embodiment and which calculates an offset of the brightness value of each voxel of the three-dimensional tomographic image volume data; and a tomographic image volume rendering section 18 which generates a three-dimensional tomographic image using a volume rendering technique for the three-dimensional tomographic image volume data offset-calculated.

On the other hand, the ultrasonic diagnostic apparatus 100 includes: a tomographic image two-dimensional coordinate transformation section 20 which generates a two-dimensional tomographic image on at least one tomographic plane of the three-dimensional tomographic image volume data on the basis of the output data from the tomographic image processing section 12; an image combining section 22 which combines the three-dimensional tomographic image generated by the tomographic image volume rendering section 18 and the two-dimensional tomographic image generated by the tomographic image two-dimensional coordinate transformation section 20; and a display section 24 as a display unit which displays an image output from the image combining section 22.

In addition, the ultrasonic diagnostic apparatus 100 includes a control panel 26 as an input interface which receives an input, such as a command from an examiner, and a control section 28 which controls each of the above components included in the ultrasonic diagnostic apparatus 100 on the basis of an input command from the control panel 26. For example, when an examiner designates an arbitrary section of the three-dimensional tomographic image volume data through the control panel 26, the information regarding the designated sectional position is transmitted to the tomographic image two-dimensional coordinate transformation section 20, and a two-dimensional tomographic image at the sectional position is generated.

Here, each of the above components will be described specifically. In the ultrasonic probe 2, transducer elements of 1 to m channels are arrayed in the long-axis direction of the ultrasonic probe. Here, when k transducer elements are also arrayed in the short-axis direction by 1 to k channels, focusing of transmitted waves or received waves in the short-axis direction is made by changing a delay time given to each of the transducer elements (1 to k channels) in the short-axis direction. In addition, transmitted waves are weighted by changing the amplitude of an ultrasonic transmission signal given to each transducer element in the short-axis direction, and received waves are weighted by changing the amplification or attenuation of an ultrasonic reception signal from each transducer element in the short-axis direction. In addition, aperture control can be performed by ON/OFF of each transducer element in the short-axis direction.

This ultrasonic probe 2 can perform three-dimensional data collection of the plural tomographic planes of the object 1 by performing scanning while moving in the short-axis direction by motor driving or manually according to a control signal from the control section 28. In addition, when k transducer elements are also arrayed in the short-axis direction by 1 to k channels, it becomes possible to collect the three-dimensional ultrasonic data by an ultrasonic beam in the short-axis direction along the curvature of the probe head or an ultrasonic beam in the short-axis direction generated by electronic focusing.

In addition, for example, cMUT (Capacitive Micromachined Ultrasonic Transducer: IEEE Trans. Ultrason. Ferroelect. Freq. Contr. Vol45 pp. 678 to 690 May 1998 and the like) in which the ultrasonic transmission and reception sensitivity, that is, an electromechanical coupling coefficient changes according to the size of a bias voltage applied in a state superimposed on a driving signal supplied from the transmission section 4 can be applied as the ultrasonic probe 2. The cMUT is a hyperfine capacitive ultrasonic transducer manufactured by a semiconductor microfabrication process (for example, LPCVD: Low Pressure Chemical Vapor Deposition).

The transmission section 4 and the receiving section 6 supply a transmission signal to the ultrasonic probe 2 and also process a received reflected echo signal. The transmission section 4 and the receiving section 6 include a transmitter circuit that controls the ultrasonic probe 2 to transmit an ultrasonic beam and a receiver circuit that receives an echo signal of the transmitted ultrasonic beam, which is reflected from the inside of the object 1, to collect the biological information and are controlled by the ultrasonic wave transmission and reception control section 8.

The phasing addition section 10 controls the phase of the reflected echo signal output from the receiving section 6 and forms an ultrasonic received beam at one point or plural convergent points. In addition, an RF signal generated by the phasing addition section 10 may be complex demodulated I and Q signals.

The tomographic image processing section 12 processes the reflected echo signal after phase addition in the phasing addition section 10 and is configured to include a signal processing circuit, which performs logarithmic compression, filtering, and image processing on the basis of reflected echo signals input sequentially, and a storage device including a magnetic disk and a RAM which stores an ultrasonic image.

The tomographic image volume data generating section 14 generates the three-dimensional tomographic image volume data on the basis of the tomographic image data of the plural tomographic planes processed by the tomographic image processing section 12. The offset calculating section 16 calculates an offset of the brightness value for each voxel of the three-dimensional tomographic image volume data. This will be described in detail later.

The tomographic image volume rendering section 18 performs two-dimensional projection processing, such as volume rendering, on the three-dimensional tomographic image volume data, for which offset calculation has been performed, to generate a three-dimensional tomographic image and transmits it to the image combining section 22.

The tomographic image two-dimensional coordinate transformation section 20 generates a two-dimensional tomographic image on at least one tomographic plane of the three-dimensional tomographic image volume data on the basis of the output data from the tomographic image processing section 12 by resampling and interpolation processing and transmits the two-dimensional tomographic image to the image combining section 22. The image combining section 22 combines the three-dimensional tomographic image generated by the tomographic image volume rendering section 18 with the two-dimensional tomographic image generated by the tomographic image two-dimensional coordinate transformation section 20 and transmits the composite image to the display section 24. The display section 24 receives the image generated by the image combining section 22 and displays the image as an ultrasonic image. The display section 24 is formed by a CRT monitor or an LCD monitor, for example.

Hereinafter, the tomographic image volume rendering section 18 of the ultrasonic diagnostic apparatus 100 of the present embodiment will be described more specifically. The tomographic image volume rendering section 18 generates a projection image (three-dimensional tomographic image) seen from at least one line-of-sight direction on the two-dimensional projection plane on the basis of the three-dimensional tomographic image volume data, and forms a three-dimensional tomographic image by multiplying the brightness value in the line-of-sight direction in the three-dimensional tomographic image volume data by the transparency value for each brightness transmitted by the control section 28. Here, expressions of the known volume rendering method used in the present embodiment are defined below.

$$C\text{out}=C\text{out}-1+(1-A\text{out}-1)\cdot Ai \cdot Ci \quad \text{(Expression 1)}$$

$$A\text{out}=A\text{out}-1+(1-A\text{out}-1)\cdot Ai \quad \text{(Expression 2)}$$

In Expression 1, Ci is an i-th voxel brightness value existing on the line of sight when the three-dimensional tomographic image volume data is viewed from a certain point on the two-dimensional projection plane generated. When data of N voxels is arrayed on the line of sight, the value Cout obtained by integration from i=0 to N−1 becomes a last output pixel value. Cout−1 indicates an integrated value up to the (i−1)-th value.

In addition, Ai in Expressions 1 and 2 is the opacity of the i-th voxel value on the line of sight, and has a value of 0.0 to 1.0. Both Cout and Aout have 0 as initial values. As shown in Expression 2, Aout is integrated (cumulatively added) each time it passes through the voxel and converges to 1.0. Therefore, as shown in Expression 1, when the integrated value Aout−1 of the opacity of voxels up to the (i−1)-th value becomes about 1.0, the i-th voxel value Ci is reflected on an output image. In addition, the transparency when the opacity is set as Ai is expressed as 1−Ai, the transparency and the opacity are complementary to each other. Accordingly, in this specification, the concept of transparency and opacity is appropriately described as transparency/opacity. Moreover, for example, even if the opacity is described, the concept of transparency is also described simultaneously.

Figure 2:
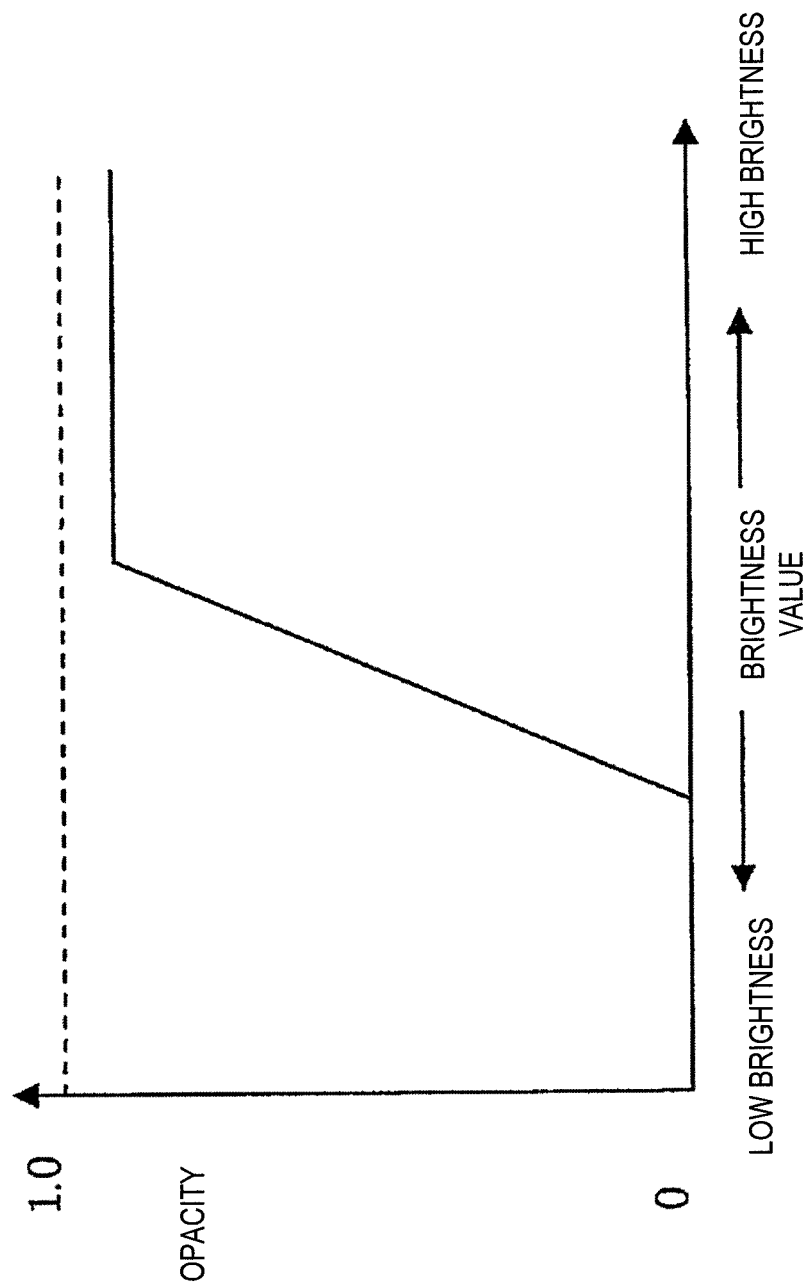
FIG. 2 is a view showing the relationship between the voxel value and the opacity.

FIG. 2 is a view showing the relationship between the voxel value and the opacity. As shown in FIG. 2, the relationship between the voxel value and the opacity is generally expressed as an opacity table in which the horizontal axis indicates a brightness and the vertical axis indicate an opacity, and the opacity is referred to from the brightness value of a voxel.

From the above, in the volume rendering processing of the present embodiment, a voxel with high opacity is regarded as a surface so that the three-dimensional tomographic image volume data can be stereoscopically displayed. In addition, a maximum value projection method of displaying only a high-brightness structure in a region of interest (maximum intensity projection), a minimum value projection method of drawing only a low-brightness structure (minimum intensity projection), a method of displaying an accumulative image of voxel values in the line-of-sight line (Ray summation), or the like is generally used as a rendering method of visualizing not the surface but the inside structure transparently.

Figure 3:
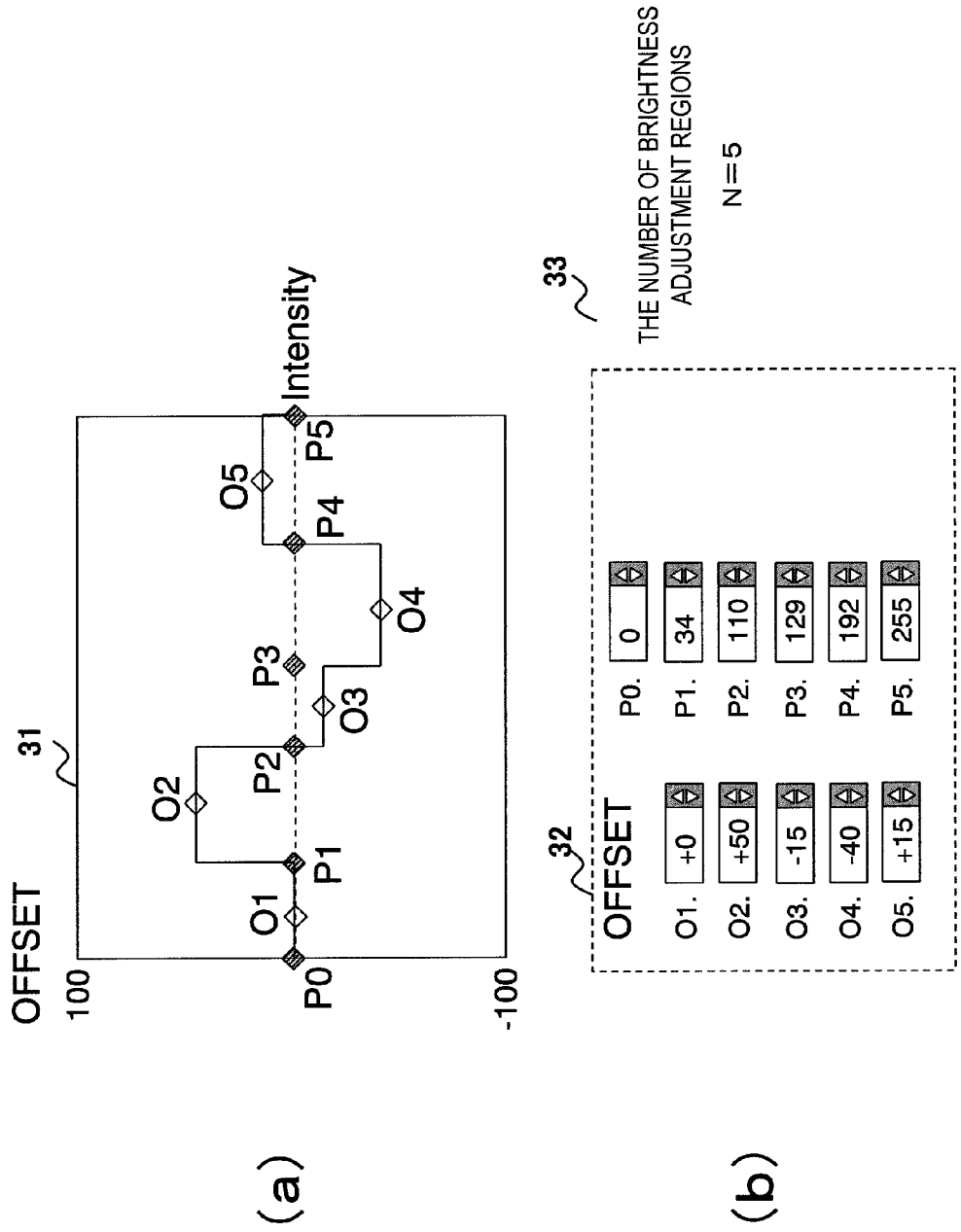
FIG. 3 is a view showing an example of a setting screen of an offset table used in an offset calculating section.

Then, a characteristic section of the ultrasonic diagnostic apparatus of the present embodiment will be described. The ultrasonic diagnostic apparatus of the present embodiment is an ultrasonic diagnostic apparatus including: the ultrasonic probe 2 which transmits or receives an ultrasonic wave to or from the object 1; the tomographic image volume data generating section 14 which generates three-dimensional tomographic image volume data on the basis of reflected echo signals of plural tomographic planes of the object 1 measured by the ultrasonic probe 2; the tomographic image volume rendering section 18 which generates a three-dimensional tomographic image seen from at least one line-of-sight direction on the two-dimensional projection plane on the basis of the three-dimensional tomographic image volume data; the display section 24 which displays a three-dimensional tomographic image; and the offset calculating section 16 which increases or decreases the brightness value of each corresponding voxel according to the brightness value of each voxel of the three-dimensional tomographic image volume data. The amount of increase or decrease in the brightness value of each voxel of the offset calculating section 16 can be adjusted through the input interface (control panel) 26, and the tomographic image volume rendering section 18 generates a three-dimensional tomographic image on the basis of the three-dimensional tomographic image volume data in which the brightness value is offset by the offset calculating section 16. FIG. 3 is a view showing an example of a setting screen of an offset table used in the offset calculating section 16. FIGS. 3(a) and 3(b) are examples of setting an offset table.

As shown in FIG. 3, boundary values (P0 to P5) for dividing a range (0 to 255) of the brightness value of each voxel of the three-dimensional tomographic image volume data into plural regions (N: 5 in the present embodiment) and the amount of increase or decrease (01 to 05) in the brightness value in each of the plural divided regions are set in the offset table.

For example, using a graph 31 shown in FIG. 3(a), the boundary of regions can be set by moving setting pointers of the boundary values expressed as P0 to P5 left and right through the control panel 26. Similarly, 01 to 05 are pointers indicating the amount of increase or decrease (offset value) in the brightness value of each region, and the offset value of each region can be set by up-and-down movement. The upper and lower limits of the graph 31 are set as 100 and −100, respectively. However, this is just an example, and any values may be set if they are in a range of input and output data. In addition, offset processing is not performed for the input brightness value removed from objects to be offset due to the movement of P0 or P5. In addition, P0 and P5 can also be fixed to both ends of the range of the brightness value of each voxel. In addition, setting of the boundary value (P0 to P5) or the amount of increase or decrease (01 to 05) in the brightness value can be performed using toggle, an encoder, an adjustment button on a liquid crystal panel, or the like.

In addition, regarding the boundary value and the amount of increase or decrease in the brightness value (offset value), 01 to 05 and P0 to P5 in a display window 32 may also be set by a pull-down menu or direct numeric value input through the control panel 26, as shown in FIG. 3(b). In addition, as shown in FIG. 3(b), the number of effective regions divided by the boundary values (P0 to P5) may be displayed as the number of brightness adjustment regions 33 (N=5).

Figure 4:
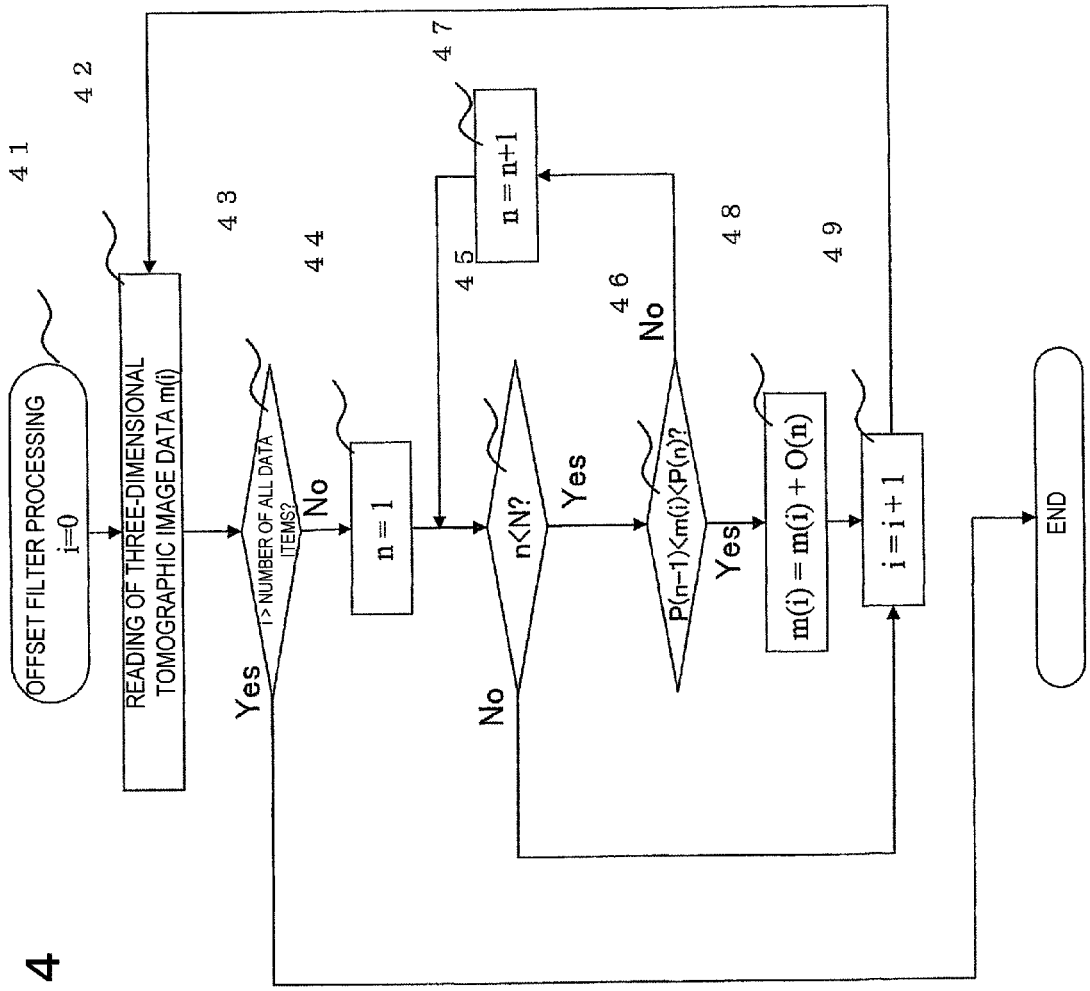
FIG. 4 is a data flow chart of brightness value conversion processing performed by the offset calculating section.

FIG. 4 is a data flow chart of brightness value conversion processing performed by the offset calculating section 16. As shown in FIG. 4, when offset filtering starts in the offset calculating section 16, a counter i is initialized to 0 (step 41). Then, the brightness value m(i) of each voxel of the three-dimensional tomographic image volume data is read (step 42). It is determined whether or not i is larger than the total number of data (the number of voxels) (step 43). If i is larger than the total number of data (Yes in step 43), the offset filtering ends. On the other hand, if i is not larger than the total number of data, that is, when offset processing is not performed for all voxels of the three-dimensional tomographic image volume data, the process proceeds to step 44 in which a counter n for region selection is initialized to 1 (step 44).

It is determined whether or not the counter n for region selection is smaller than the number of brightness adjustment regions N (step 45). If the counter n for region selection is smaller than the number of brightness adjustment regions N (Yes in step 45), it is determined whether or not the i-th read brightness value m(i) of the three-dimensional tomographic image volume data is in a range of P(n−1) to P(n) (step 46). If Yes in step 46, the amount of increase or decrease (offset value) O(n) in the brightness value is added in step 48 (step 48). On the other hand, if No in step 46, the counter n for region selection is updated and the process returns to step 45 (step 47). That is, by the loop of steps 45 to 47, the read i-th brightness value m(i) of the three-dimensional tomographic image volume data is classified into one of the regions divided by the boundary values P(0) to P(N), and the amount of increase or decrease (offset value) O(n) in the brightness value corresponding to the divided region is added in step 48. After the end of step 48 or if No in step 45, the counter i is updated and the process returns to step 42 (step 49).

Through the above processing, the amount of increase or decrease (offset value) O(n) in the brightness value in each of the regions divided by the boundary values P(0) to P(N) is added to the brightness values of all voxels of the three-dimensional tomographic image volume data. In addition, although the case of performing offset processing using an offset table is shown in the present embodiment, the present invention is not limited to this. For example, it is also possible to make the offset calculating section set a function of outputting the amount of increase or decrease in the brightness value according to the input of the brightness value of each voxel of the three-dimensional tomographic image volume data and increase or decrease the brightness value of each voxel on the basis of this function.

Figure 5:
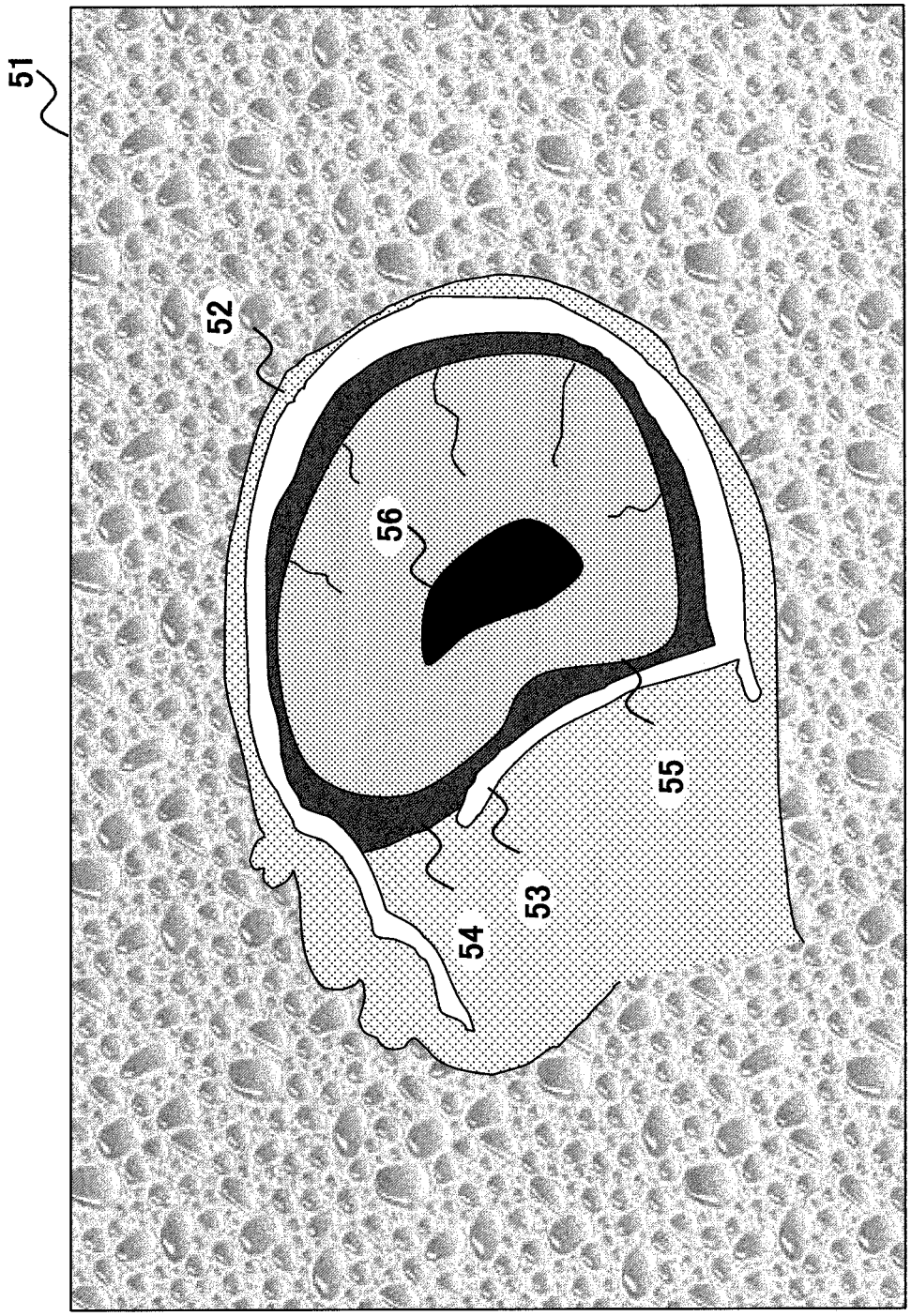
FIG. 5 is a schematic view showing a tomographic image of the fetal head expressed as brightness values of 256 gray-scale levels.

Next, an example of application of the offset calculating section 16 of the present embodiment to the object 1 and the effect will be described. FIG. 5 is a schematic view showing a tomographic image of the fetal head expressed as brightness values of 256 gray-scale levels. In a tomographic image 51, it is assumed that the brightness value of periderma 52 is 128. In addition, it is assumed that the brightness value of a fetal skull 53 is 200 and the brightness value of a lumen region of skull 54 is 32. In addition, it is assumed that the brightness value of brain substance 55 is 80 and the brightness value of a ventricle 56 is 16. In addition, it is assumed that the background around the fetal head is not considered in order to explain the effect easily.

Figure 6:
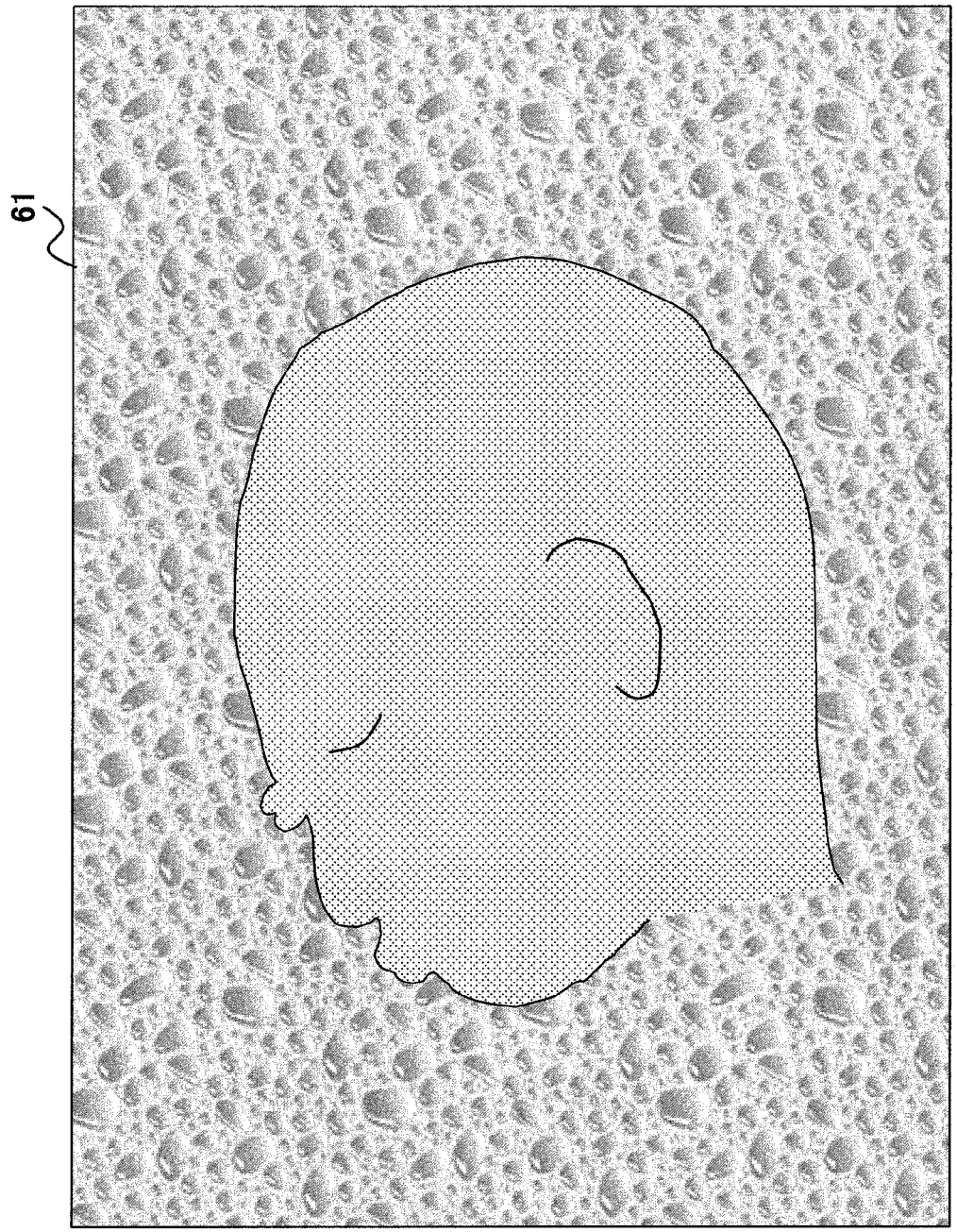
FIG. 6 is a schematic view showing a three-dimensional tomographic image after performing volume rendering on the three-dimensional tomographic image volume data of the fetal head according to general opacity setting.

FIG. 6 shows a three-dimensional tomographic image at the time of general opacity setting, in which a high-brightness portion is set opaquely and a low-brightness portion is set transparently, when building a three-dimensional tomographic image for three-dimensional tomographic image volume data, which is a group of tomographic images, by volume rendering. As shown in FIG. 6, in a three-dimensional tomographic image 61, a three-dimensional surface image obtained by rendering of the surface of the fetal head, in which most of the output brightness is determined by the high-brightness periderma 52 and the fetal skull 53, is formed.

Figure 7:
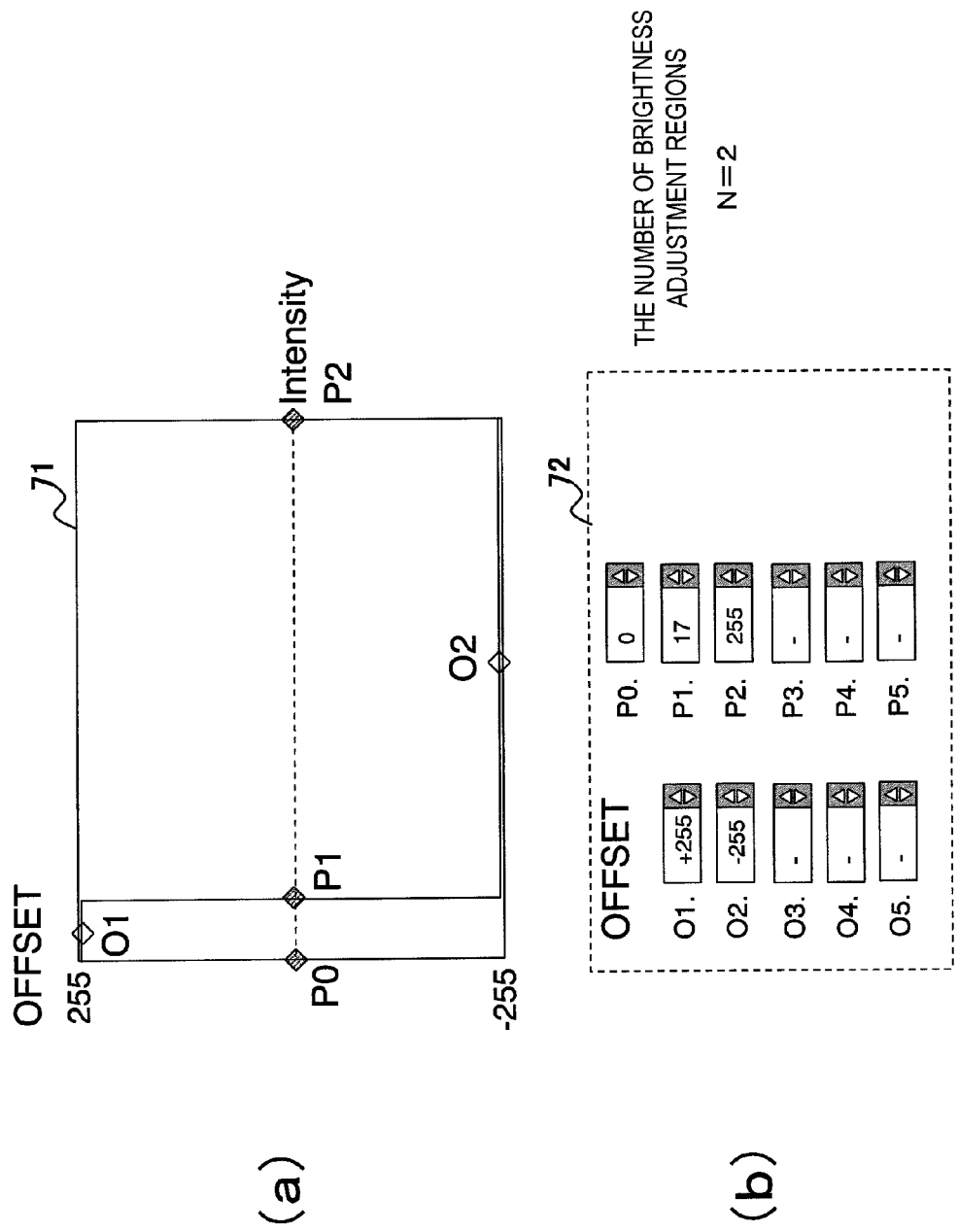
FIG. 7 is a setting example of an offset table when it is necessary to enhance the visibility of the ventricle.

On the other hand, using the offset calculating section 16 of the present embodiment, an offset table is set as shown in FIG. 7 when it is necessary to enhance the visibility of the ventricle 56 as specific tissue that the examiner wants. That is, the offset table includes a graph 71 shown in FIG. 7(a) and a display window 72 shown in FIG. 7(b). In this case, the number of adjustment regions N is 2, and P0 and P2 are maximum and minimum values of the input brightness and are fixed values. In addition, in order to display only a desired specific target portion, setting the amount of increase or decrease (offset value) 01 in the brightness value added to the target portion to 255 and setting the amount of increase or decrease (offset value) 02 of the brightness value added to portions other than the target portion to −255 are a method of displaying the target portion most extremely in a three-dimensional manner. Since the boundary value P1 is set while checking an image, the boundary value P1 can be set through the control panel 26 by the examiner.

Figure 8:
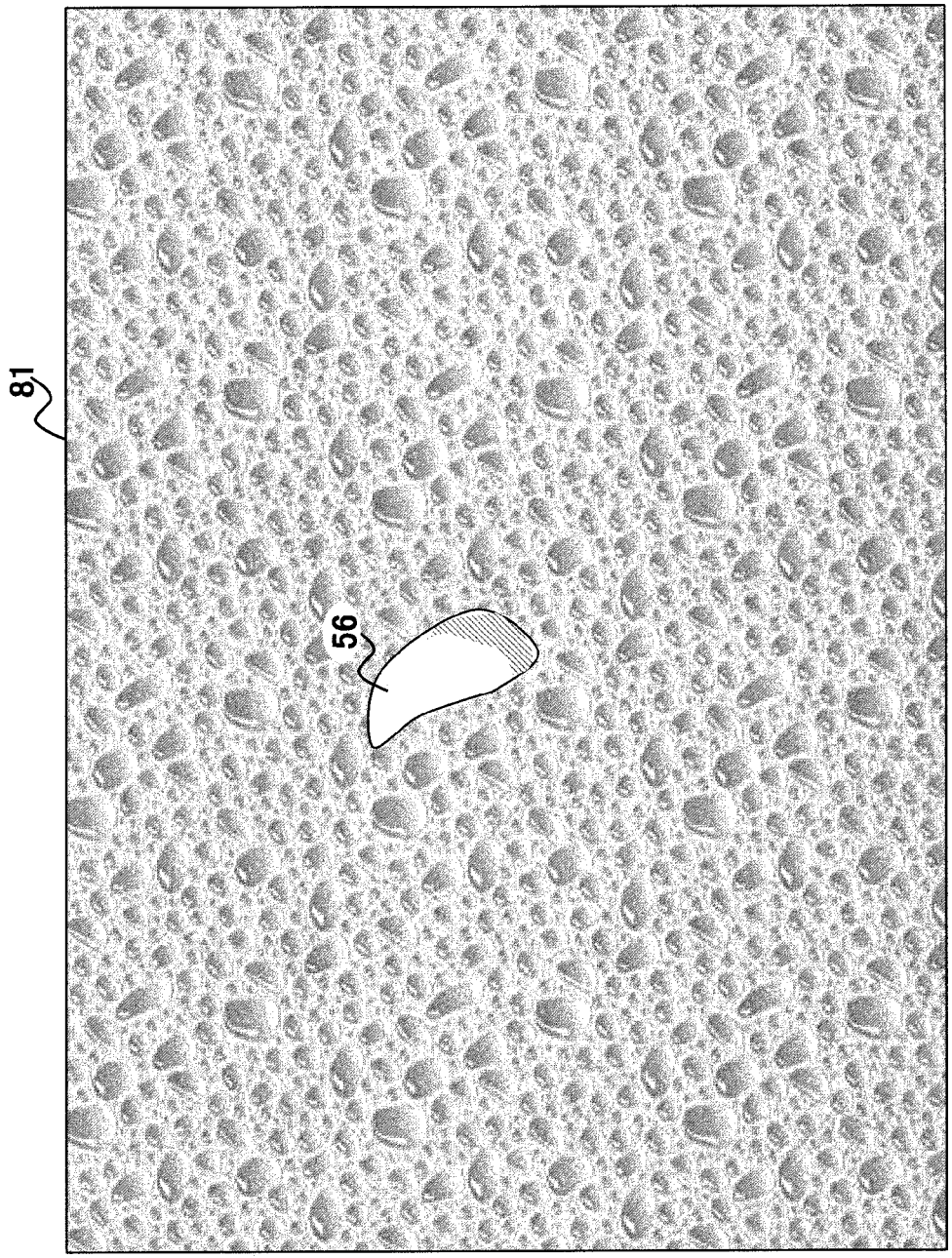
FIG. 8 is a schematic view of a three-dimensional tomographic image generated on the basis of the three-dimensional tomographic image volume data offset-calculated by the offset calculating section on the basis of the offset table shown in FIG. 7.

FIG. 8 is a schematic view of a three-dimensional tomographic image generated on the basis of three-dimensional tomographic image volume data offset-calculated by the offset calculating section 16 on the basis of the offset table shown in FIG. 7. Since the brightness value of the ventricle 56 is 16 which is in a range of P0(0) to P1(17), an offset of +255 is made. Since other tissue is in a range of P1(17) to P2(255), an offset of −255 is made. Accordingly, as shown in FIG. 8, a three-dimensional tomographic image 81 is generated and displayed as a three-dimensional tomographic image in which the visibility of the ventricle 56 is enhanced. Moreover, when highlight display from the smallest brightness value to the arbitrary brightness value is necessary as in this example, the three-dimensional tomographic image shown in FIG. 8 can be generated with a simple operation by arbitrarily setting a parameter "display threshold value" and the amount of increase or decrease (offset value) in the brightness value using toggle, an encoder, an adjustment button on a liquid crystal panel, or the like.

Figure 9:
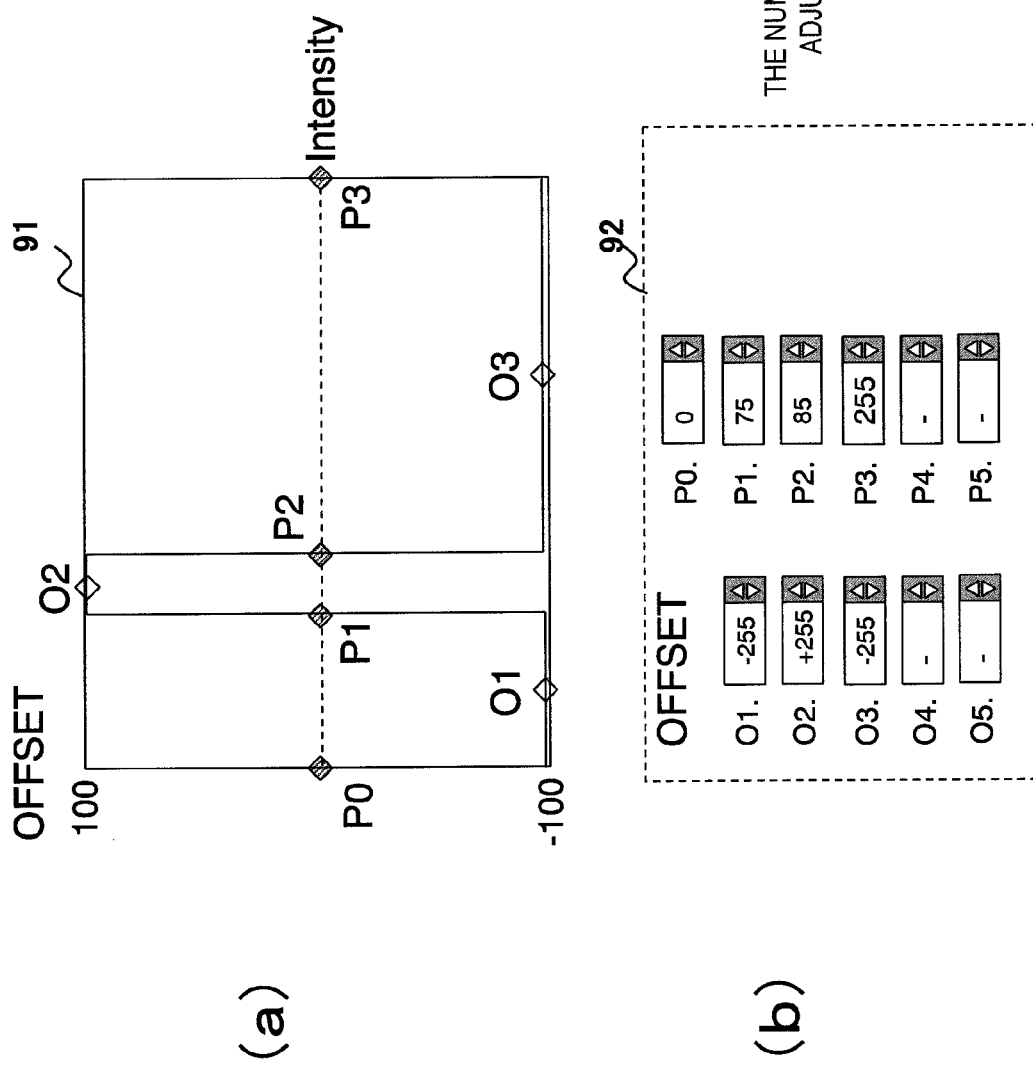
FIG. 9 is a setting example of an offset table when it is necessary to enhance the visibility of the brain substance.

On the other hand, when it is necessary to enhance the visibility of the brain substance 55 as specific tissue that the examiner wants, an offset table is set as shown in FIG. 9. That is, as shown in FIG. 5, the ventricle 56 with low brightness is present inside the brain substance 55, the lumen region of skull 54 with low brightness similar to the above is present around the brain substance 55, and the fetal skull 53 is present around the lumen region of skull 54. Accordingly, the brightness range with the enhanced visibility is one region with intermediate brightness. Therefore, in the offset table, as in a graph 91 shown in FIG. 9(a) and a display window 92 shown in FIG. 9(b), it is assumed that the number of adjustment regions N is 3, P0 and P3 are fixed to minimum and maximum values of the input brightness, and the amount of increase or decrease (offset value) in the brightness value is set to 01=−255, 02=255, and 03=−255. The boundary values P1 and P2 can be arbitrarily set through the control panel 26 while checking the image.

Figure 10:
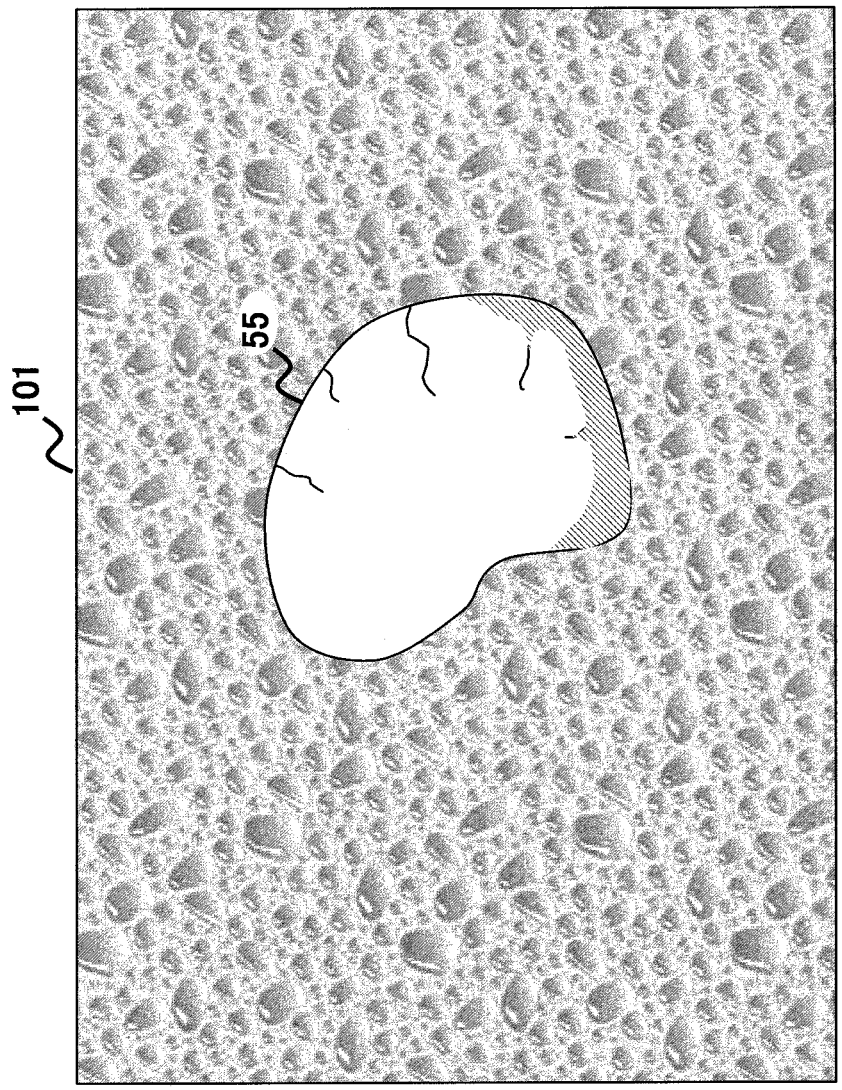
FIG. 10 is a schematic view of a three-dimensional tomographic image generated on the basis of the three-dimensional tomographic image volume data offset-calculated by the offset calculating section on the basis of the offset table shown in FIG. 9.

FIG. 10 is a schematic view of a three-dimensional tomographic image generated on the basis of three-dimensional tomographic image volume data offset-calculated by the offset calculating section 16 on the basis of the offset table shown in FIG. 9. Since the brightness value of the brain substance 55 is 80 which is in a range of P1(75) to P2(85), an offset of +255 is made. Since other tissue is in a range of P0(0) to P1(75) or a range of P2(85) to P3(255), an offset of −255 is made. Accordingly, as shown in FIG. 10, a three-dimensional tomographic image 101 is generated and displayed as a three-dimensional tomographic image in which the visibility of the brain substance 55 is enhanced. Moreover, when it is necessary to highlight an arbitrary brightness range corresponding to the intermediate brightness as in this example, the three-dimensional tomographic image shown in FIG. 10 can be generated with a simple operation by arbitrarily setting parameters "display start threshold value" and "display end threshold value" and the amount of increase or decrease (offset value) in the brightness value using toggle, an encoder, an adjustment button on a liquid crystal panel, or the like.

In addition, since setting using toggle or an encoder is difficult when there are two or more desired specific tissue portions (target portions), it is preferable to edit a setting screen on the display screen directly. An increase or decrease in the number of brightness adjustment regions N on the liquid crystal panel on the display from the control panel 26, the boundary values P0 to Pn, and offsets O0 to On can be set by a track ball operation in the control panel 26 or a touch panel on the display section 24. In addition, they may also be set by the control panel 26 using a pull-down menu (up-and-down bar) in the display window 32.

In addition, although the example in which an examiner adjusts the offset table through the control panel 26 is shown in the present embodiment, the present invention is not limited to this. For example, plural offset tables, such as an offset table for enhancing the visibility of tissue with low brightness value, an offset table for enhancing the visibility of tissue with intermediate brightness value, and an offset table for enhancing the visibility of tissue with high brightness value, may be prepared as default and an examiner may select an offset table to be used. According to this, the examiner can obtain a three-dimensional tomographic image, in which the visibility of desired specific tissue is enhanced, with a simple operation.

Figure 11:
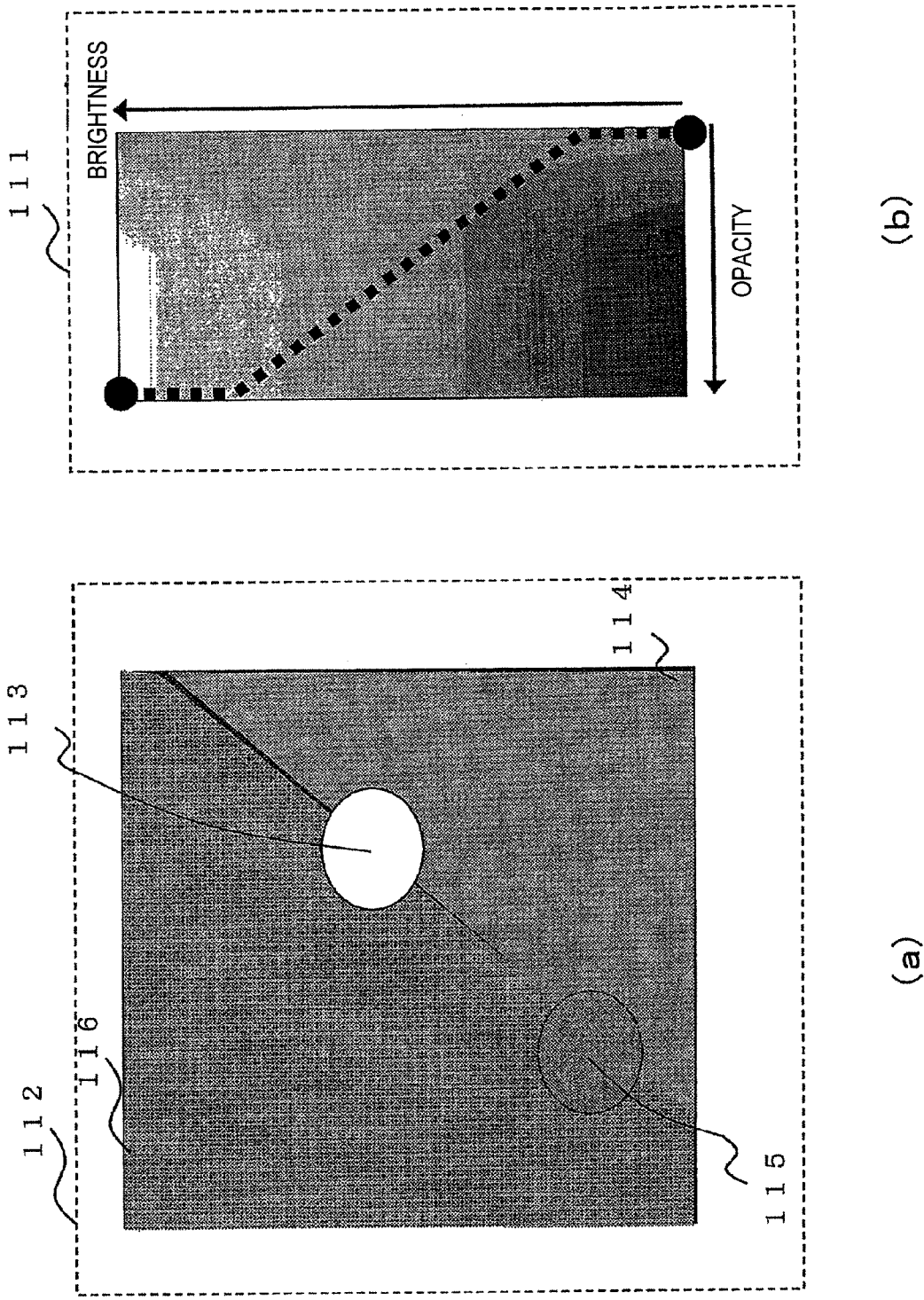
FIG. 11 is a view showing a display example of a two-dimensional tomographic image and a brightness-opacity map.

Then, a two-dimensional tomographic image as an auxiliary screen when setting an offset table will be described using FIGS. 11 to 13. FIG. 11 is a view showing a display example of a two-dimensional tomographic image and a brightness-opacity map. FIG. 11(a) shows a two-dimensional tomographic image, and FIG. 11(b) shows a brightness-opacity map. As shown in FIG. 11(b), in a brightness-opacity map 111, a color code using a two-dimensional table in which the vertical axis indicates brightness and the horizontal axis indicates opacity is set. That is, the color code is set according to the brightness value and the transparency/opacity. Moreover, in a two-dimensional tomographic image 112, a color is given according to the color code of the brightness-opacity map 111, as shown in FIG. 11(a). A dotted line in the brightness-opacity map 111 is equivalent to the line showing the relationship between the voxel value and the opacity shown in FIG. 2, the opacity with respect to the input brightness value is determined uniquely, and the color of a pixel displayed on the two-dimensional tomographic image 112 is determined at one point on the dotted line of the brightness-opacity map 111.

The tomographic image data as the basis of the two-dimensional tomographic image 112 is generated by the tomographic image two-dimensional coordinate transformation section 20. The tomographic image data is tomographic image data of the arbitrary section of the three-dimensional tomographic image volume data designated through the control panel 26 by the examiner, and offset processing by the offset calculating section 16 is not performed on the tomographic image data. The tomographic image data is input to the image combining section 22. The image combining section 22 acquires from the control section 28 the boundary value of the offset table, the amount of increase or decrease (offset value) in the brightness, and the brightness-opacity map 111.

The image combining section 22 offsets the brightness value of the tomographic image data input from the tomographic image two-dimensional coordinate transformation section 20 on the basis of the offset table and converts a color of each voxel of the offset tomographic image data on the basis of the brightness-opacity map 111 to generate a two-dimensional tomographic image. For example, conversion into numeric value with color information, such as RGB or YUV is performed referring to the brightness value and the opacity of each voxel of the tomographic image data in which the brightness value has been offset. In such color code conversion processing, by setting the brightness value on the vertical axis like the brightness-opacity map 111 and setting color data with a high chroma, which is not relevant to the input data, as the opacity decreases on the horizontal axis, it is possible to display a transmissive region, a non-transmissive region, and an intermediate region in a three-dimensional tomographic image in a stepwise manner.

For example, in FIG. 11, in the two-dimensional tomographic image 112, an opaque region 113 dominant in a three-dimensional tomographic image, an intermediate region 114 with low transparency having a large effect on a three-dimensional tomographic image, an intermediate region 115 with high transparency having little effect on a three-dimensional tomographic image, and a transparent region 116 having no effect on a three-dimensional tomographic image are displayed after being encoded with different hues from the brightness. As a result, since the examiner can grasp intuitively the influence of the boundary value and the amount of increase or decrease (offset value) in the brightness value on the three-dimensional tomographic image, the examination efficiency can be improved. That is, the examiner can recognize which region on the two-dimensional tomographic image 112 is reflected on the three-dimensional tomographic image and which region is not reflected. For example, since a region of the transparent region 116 is not reflected on the three-dimensional tomographic image in current setting of the offset table, it can be seen that the setting of the offset table should be adjusted if it is reflected.

Figure 12:
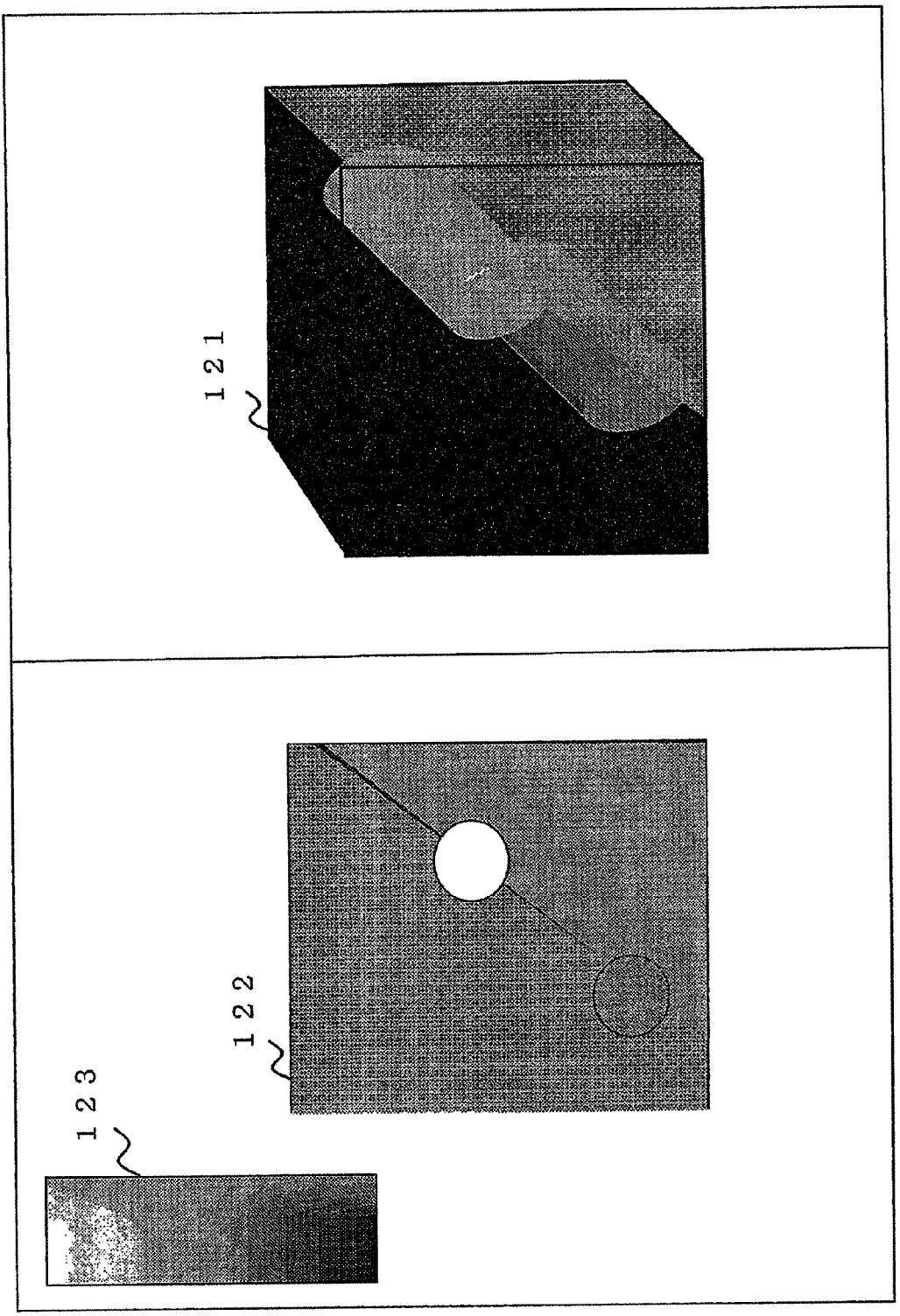
FIG. 12 is a view showing a display example of a three-dimensional tomographic image, a two-dimensional tomographic image, and a brightness-opacity map.

FIG. 12 is a view showing a display example of a three-dimensional tomographic image, a two-dimensional tomographic image, and a brightness-opacity map. As shown in FIG. 12, a three-dimensional tomographic image 121, a two-dimensional tomographic image 122, and a brightness-opacity map 123 are displayed side by side. Referring to FIG. 12, the examiner can recognize that the opaque region 113 is drawn opaquely, the transparent region 116 is not drawn at all, and the intermediate regions 114 and 115 are drawn translucently. In addition, a target portion can be clearly visualized by emphasizing the opaque region 113.

Figure 13:
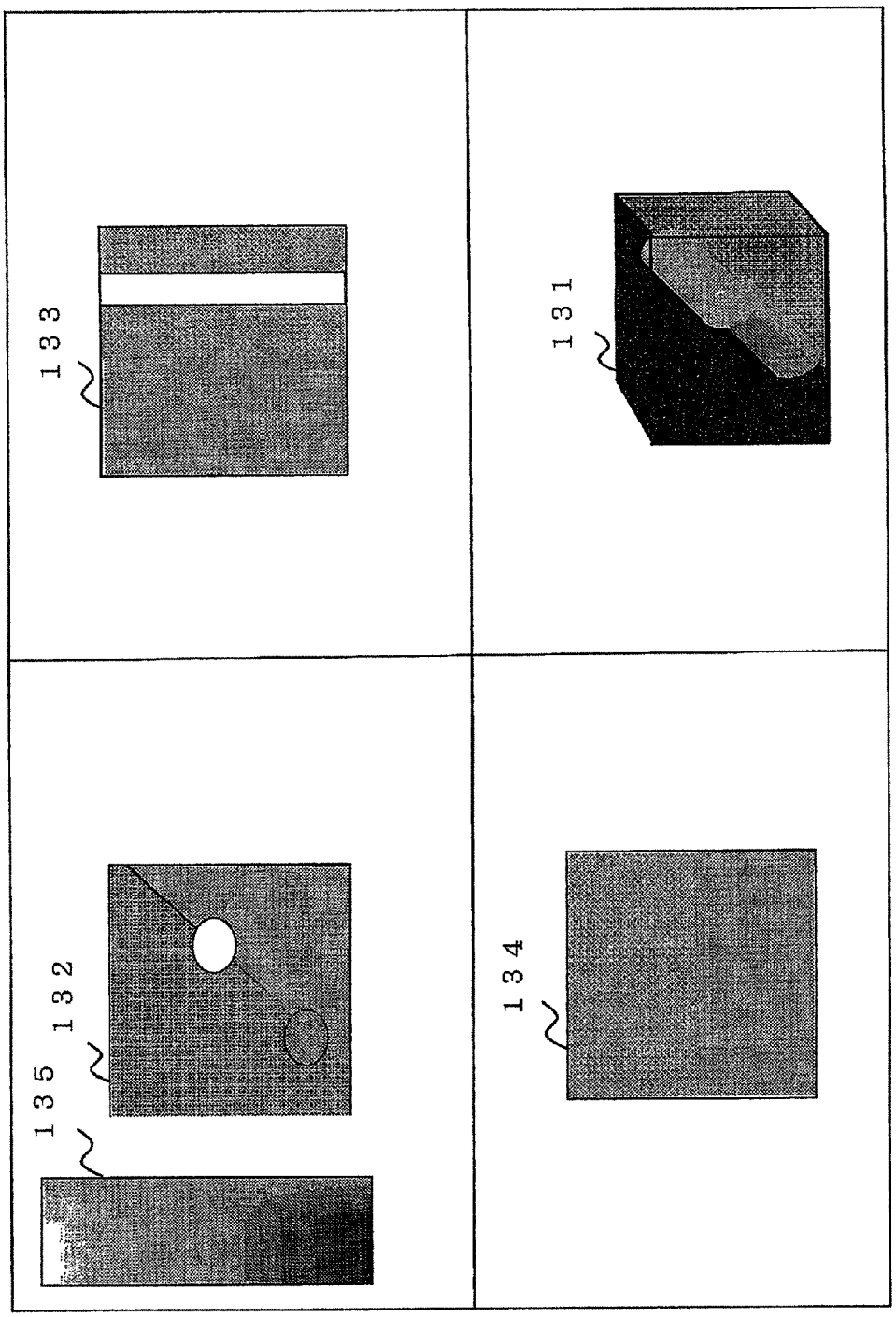
FIG. 13 is a view showing a display example of a three-dimensional tomographic image, a two-dimensional tomographic image, and a brightness-opacity map.

FIG. 13 is a view showing a display example of a three-dimensional tomographic image, a two-dimensional tomographic image, and a brightness-opacity map. As shown in FIG. 13, a three-dimensional tomographic image 131, a two-dimensional tomographic image 132 on the X-Y tomographic plane, a two-dimensional tomographic image 133 on the X-Z tomographic plane, a two-dimensional tomographic image 134 on the Y-Z tomographic plane, and a brightness-opacity map 135 are displayed side by side. By displaying the sections simultaneously from three directions as described above, it is possible to enable the examiner to understand the visualization region more clearly.

Figure 14:
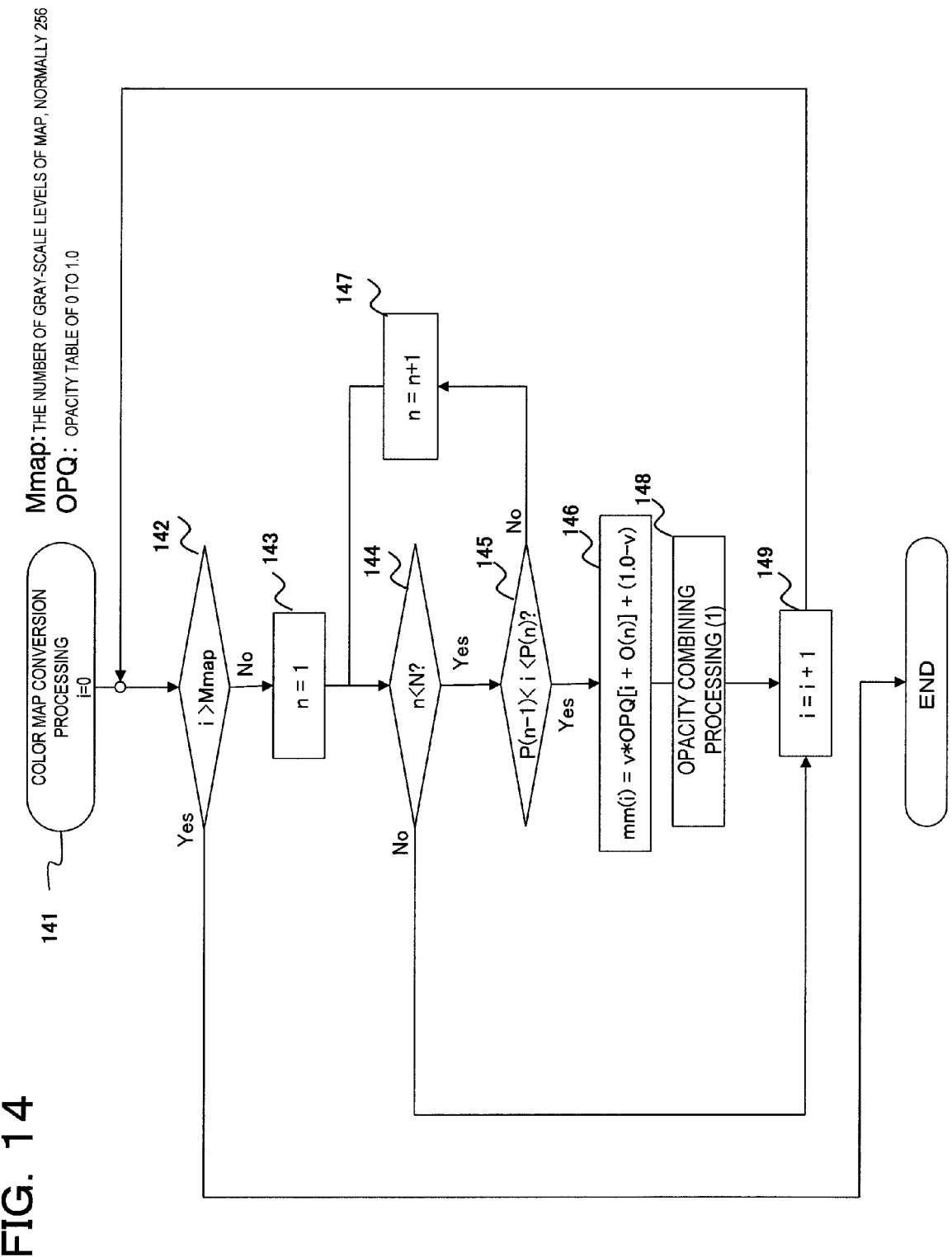
FIG. 14 is a view showing the flow of creating a color conversion table.

Then, an example of a method of creating a color conversion table (brightness-opacity map) used in the above color code conversion processing will be described using FIGS. 14 to 16. FIG. 14 is a view showing the flow of creating a color conversion table. It is assumed that symbols P and O described in FIG. 14 indicate the above-described boundary value P(n) and the amount of increase or decrease (offset value) O(n) in the brightness value, respectively.

Figure 15:
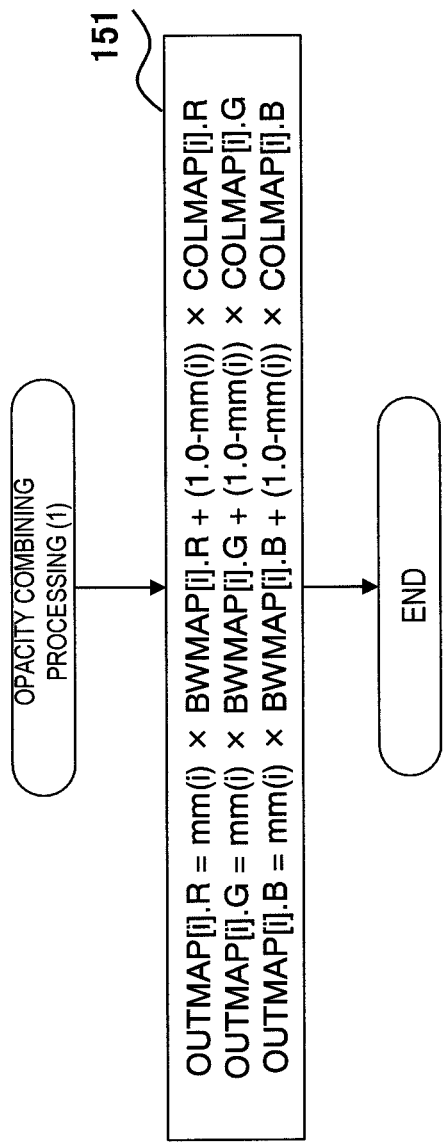
FIG. 15 is a view showing an example of processing of creating a combined color map table OUTMAP[i] in step 148.
Figure 16:
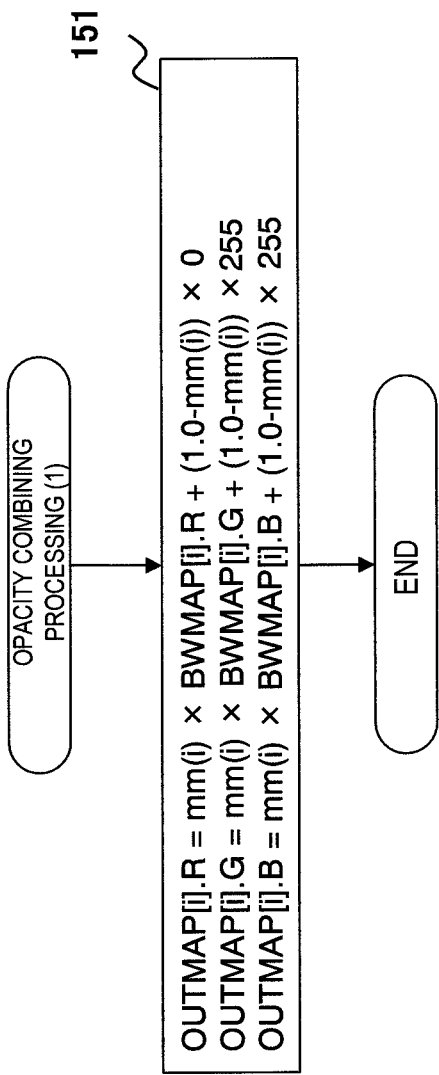
FIG. 16 is a view showing an example of processing of creating a combined color map table OUTMAP[i] in step 148.

Moreover, in FIGS. 15 and 16, a color conversion table OUTMAP[i] used in the present embodiment indicates a combined color map table, BWMAP[i] indicates an RGB conversion table for tomographic image output, and COLMAP[i] indicates an RGB color table for transparency setting. These are tables for performing conversion into natural colors by returning three elements of R, G, and B, which are three primary colors, to the input i, and each table is a color map table accessible to three elements of RGB by *.R, *.G, and *.B. i indicates a gray-scale level according to the input brightness. 256 gray-scale levels of 0 to 255 are used in many cases, but any number may be used.

In the RGB table for transparency setting COLMAP, for example, *.R=0, *.G=255, and *.B=0 may be set for all gradation elements i and becoming green according to an increase in transparency may be set, or an arbitrary visual effect may be given by setting different hues, chroma, and brightness for the gradation element i.

As shown in FIG. 14, when color map conversion processing starts, the input gradation value (indicating the input brightness value, the value of elasticity, or other inputs) expressed by the counter i is initialized to 0 (step 141). Then, size comparison between the counter i and Mmap (the number of gray-scale levels of a map) is performed (step 142). If i is smaller than Mmap (No in step 142), the process proceeds to step 143. The counter for region selection n is initialized to 1 in step 143, the selected input gradation value i is classified into one of the regions divided by the boundary values P(0) to P(N) in steps 144 and 145, opacity mm(i) is calculated with reference to an opacity table OPQ[n] using a value obtained by adding the amount of increase or decrease (offset value) O(n) in the brightness value selected in step 146 to i, and a combined color map table OUTMAP[i] is created using the opacity mm(i) in step 148.

A constant v used in step 146 is a parameter for having an effect of an opaque color, and is normally set to 1.0. Steps 143 and 147 are initialization processing and update processing of the counter n for region selection, respectively, and step 149 is update processing of the counter i.

FIG. 15 is a view showing an example of the processing of creating the combined color map table OUTMAP[i] in step 148. As shown in FIG. 15, in step 151, each element of OUTMAP[i] is calculated as a value obtained by adding a value, which is obtained by multiplication of BWMAP[i] and mm(i), and a value, which is obtained by multiplication of COLMAP [i] and (1.0-mm(i)).

This indicates that the color map table OUTMAP[i] is created in which when *.R=0, *.G=255, and *.B=0 are set for all gradation elements i in the RGB table COLMAP for transparency setting, the tomographic image brightness BWMAP [i] is output as it is in the case of the opaque input gradation value i and a tomographic image becoming gradually green according to a decrease in opacity is output in the case of the transparent input gradation value i, for example.

That is, a region of a tomographic image formed as an opaque three-dimensional voxel is displayed in black and white or a tomographic image with a set color tone is displayed, a region of a tomographic image formed as a transparent three-dimensional voxel is displayed with a color for transparency setting other than the set color tone, and the color for transparency setting is displayed with a high ratio on the tomographic image according to change from opacity to transparency.

At this time, although a completely green color appears in the case of the completely opaque input gradation value i, the constant v used in step 146 is set to 1.0 or less (for example, 0.9 or 0.8) so that it is possible to adjust the condition of coloring, such as translucence. Accordingly, since the region of the completely opaque input gradation value i becomes translucent green instead of complete green, the examiner can recognize the shape of the region and the like visually.

FIG. 16 is a view showing an example of the processing of creating the combined color map table OUTMAP[i] in step 148. In step 161, the RGB color table for transparency setting is not prepared, and the combined color map table OUTMAP is created in a simple way by calculating a composite color with the fixed color value for transparency setting using the opacity coefficient mm(i).

The above-described two examples are examples of a method of combining each element of the RGB color map with the opacity coefficient mm(i). However, it is also possible to store the color information in the HSV format, in which the chroma, brightness, and hue are stored as parameters, and to perform combining processing using those obtained by changing these parameters by mm(i). The output format is not limited to the RGB format, and a YIN method may also be used.

(Second Embodiment)

Figure 17:
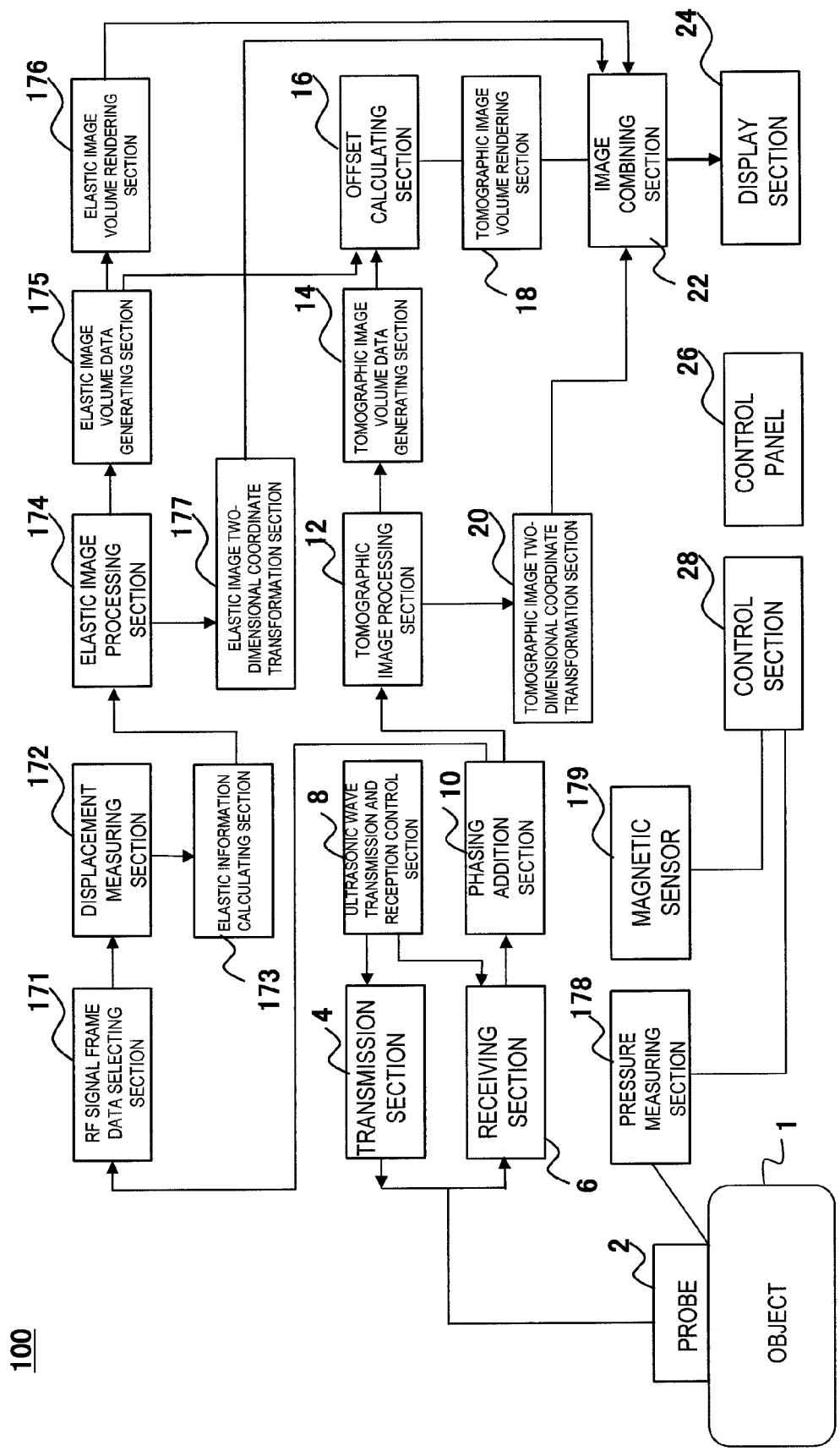
FIG. 17 is a block diagram showing the configuration of an ultrasonic diagnostic apparatus of a second embodiment.

A second embodiment of an ultrasonic diagnostic apparatus to which the present invention is applied will be described with reference to the drawings. FIG. 17 is a block diagram showing the configuration of the ultrasonic diagnostic apparatus of the second embodiment. The same configuration as in the first embodiment will not be described.

As shown in FIG. 17, the ultrasonic diagnostic apparatus 100 includes: an RF signal frame data selecting section 171 which stores RF signal frame data output from the phasing addition section 10 and which selects at least two items of the frame data; a displacement measuring section 172 which measures the displacement of body tissue of an object; an elastic information calculating section 173 which calculates the distortion or the elastic modulus from the displacement information measured by the displacement measuring section 172; an elastic image processing section 174 which forms a color elastic image from the distortion or the elastic modulus calculated by the elastic information calculating section 173; and an elastic image two-dimensional coordinate transformation section 177 which converts an output signal from the elastic image processing section 174 so as to fit the display of the display section 24.

In addition, the ultrasonic diagnostic apparatus 100 includes an elastic image volume data generating section 175 which generates elastic image volume data by performing coordinate transformation to three-dimensional elastic data on the basis of an output signal from the elastic image processing section 174 and an elastic image volume rendering section 176 which performs volume rendering, maximum and minimum values projection, or averaging processing on the elastic image volume data, which is present in the line-of-sight direction of each pixel on the two-dimensional projection plane, on the basis of an output signal from the elastic image volume data generating section 175.

The RF signal frame data selecting section 171 stores plural RF signal frame data items from the phasing addition section 10 and selects a pair of RF signal frame data items, that is, two items of the RF signal frame data from the stored RF signal frame data group. For example, RF signal frame data from the phasing addition section 10 generated in time series, that is, on the basis of the frame rate of an image is sequentially stored in the RF signal frame data selecting section 171, and the stored RF signal frame data (N) is selected as first data and at the same time, one RF signal frame data item (X) is selected from the RF signal frame data group (N−1, N−2, N−3, . . . , N−M) previously stored. In addition, N, M, and X herein are index numbers given to the RF signal frame data, and are assumed to be natural numbers.

In addition, the displacement measuring section 172 performs one-dimensional or two-dimensional correlation processing on a pair of selected data, that is, the RF signal frame data (N) and the RF signal frame data (X) to calculate a displacement or movement vector in body tissue corresponding to each point of the tomographic image, that is, one-dimensional or two-dimensional displacement distribution regarding the displacement direction and size. Here, a block matching method is used to detect a movement vector. The block matching method is to perform processing in which an image is divided into blocks with, for example, "N×N" pixels, a block in a region of interest is observed, the most similar block to the observed block is searched for from previous frames, and a sample value is determined by predictive coding, that is, by the difference referring to this.

The elastic information calculating section 173 calculates the distortion or the elastic modulus of body tissue corresponding to each point on the tomographic image from the measurement value output from the displacement measuring section 172, for example, the movement vector and the pressure value, which is output from a pressure measuring section 178, and generates an elastic image signal, that is, elastic frame data, on the basis of the distortion or the elastic modulus.

In this case, the data of the distortion is calculated by spatial differentiation of the amount of movement of body tissue, for example, by spatial differentiation of the displacement. In addition, in the configuration with a pressure measuring function as shown in the pressure measuring section 178, the elastic modulus can be calculated and the elastic modulus may also be used as elastic data accordingly. The data of the elastic modulus is calculated by dividing the pressure change by a distortion change. For example, assuming that the displacement measured by the displacement measuring section 172 is L(X) and the pressure measured by the pressure measuring section 178 is P(X), distortion $\Delta S(X)$ can be calculated by spatial differentiation of L(X). Accordingly, the distortion $\Delta S(X)$ can be calculated using Expression $\Delta S(X)=\Delta L(X)/\Delta X$. In addition, the Young's modulus Ym(X) of elastic modulus data is calculated by Expression of $Ym=(\Delta P(X))/\Delta S(X)$. Since the elastic modulus of body tissue corresponding to each point of the tomographic image is calculated from this Young's modulus Ym, it is possible to acquire the two-dimensional elastic image data continuously. In addition, the Young's modulus is a ratio of simple tensile stress applied to the object to the tensile strain occurring in parallel to the tensile stress.

The elastic image processing section 174 is configured to include a frame memory and an image processing section. The elastic image processing section 174 secures the elastic frame data, which is output in time series from the elastic information calculating section 173, in the frame memory and performs image processing on the secured elastic frame data. In addition, the elastic image processing section 174 evaluates an error of an elastic image from the output information of the RF signal frame data selecting section 171, the displacement measuring section 172, or the elastic information calculating section 173 and performs masking of the output image.

The elastic image two-dimensional coordinate transformation section 177 performs coordinate transformation of the elastic frame data from the elastic image processing section 174 so as to fit the monitor. In addition, the ultrasonic probe 2 can perform scanning in the short-axis direction manually or by motor driving according to a control signal from the control section 28. In addition, in the case of a configuration including a magnetic sensor 179 even if manual scanning is performed, it is possible to detect the amount of compression or the short axis position by using the positional information from the magnetic sensor 179.

The elastic image volume data generating section 175 performs coordinate transformation to the three-dimensional elastic data from the elastic image processing section 174, and the elastic image volume rendering section 176 performs volume rendering, maximum and minimum values projection, or average processing on the output volume data present in the line-of-sight direction of each pixel on the two-dimensional projection plane.

The image combining section 22 combines a tomographic image with the tomographic data and the distortion/elastic data generated by the elastic image volume rendering section. The brightness information and the hue information regarding each pixel of the composite image are for generating an image displayed on the display section 24 by adding information on a monochrome tomographic image and information on a color elastic image with a mixing ratio and performing RGB conversion.

Here, the offset calculating section 16 converts the brightness of the three-dimensional tomographic image volume data output from the tomographic image volume data generating section 14 using the three-dimensional elastic image data and transmits the three-dimensional tomographic image volume data to the tomographic image volume rendering section 18. In other words, the offset calculating section 16 of the present embodiment increases or decreases the brightness value of each corresponding voxel of the three-dimensional tomographic image volume data, which is output from the tomographic image volume data generating section 14, according to the value of elasticity of each voxel of the three-dimensional elastic image volume data output from the elastic image volume data generating section 175.

In addition, the elastic image data is a generic term for elastic parameters indicating the stiffness, such as the strain, Young's modulus, longitudinal modulus, and transverse modulus calculated by the method described above, and is assumed not to indicate a specific one.

Figure 18:
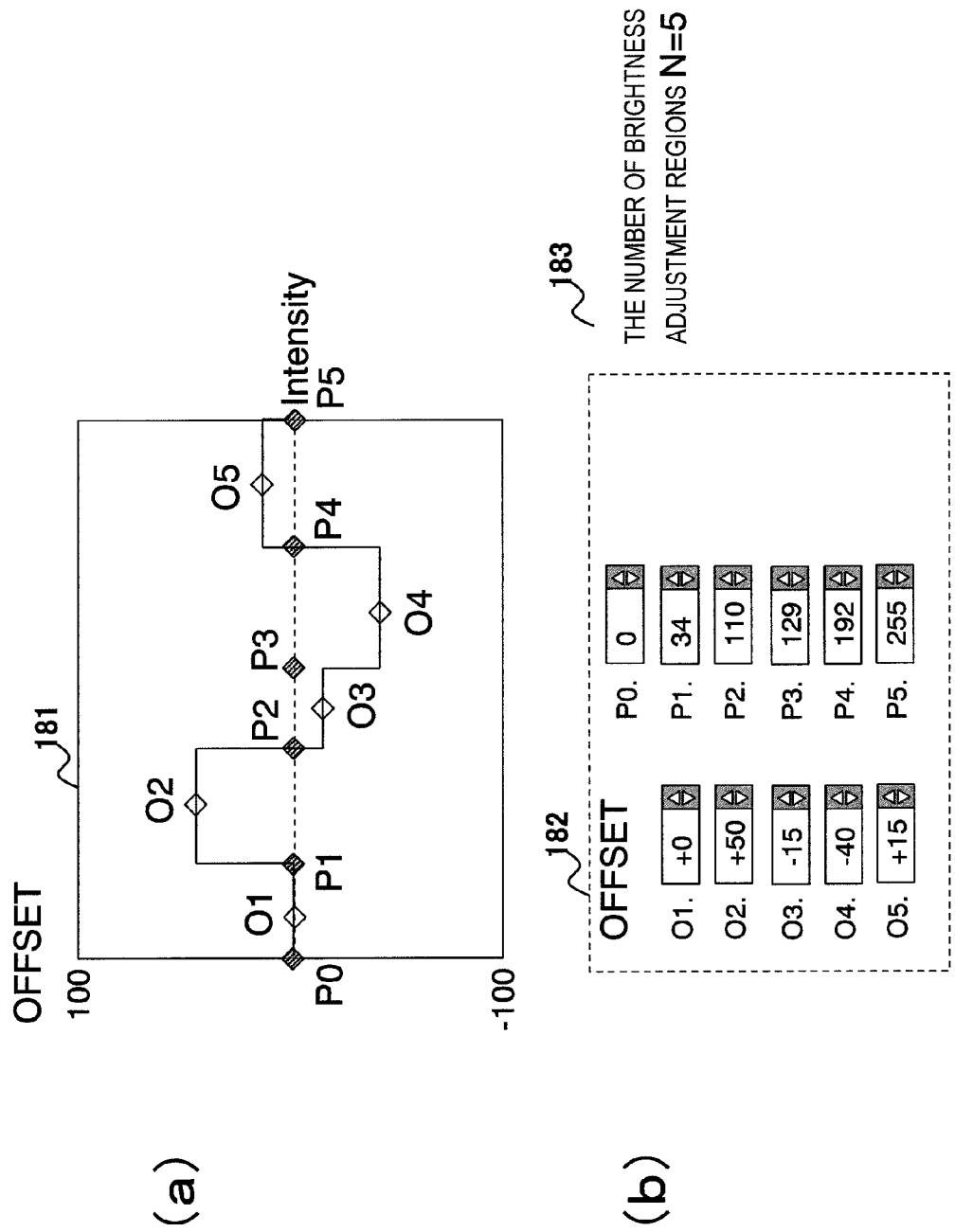
FIG. 18 is a view showing an example of a setting screen of an offset table used in an offset calculating section.

Then, a characteristic section of the ultrasonic diagnostic apparatus of the present embodiment will be described. FIG. 18 is a view showing an example of a setting screen of an offset table used in the offset calculating section 16. FIGS. 18(*a*) and 18(*b*) are examples of setting an offset table.

As shown in FIG. 18, boundary values (E0 to E5) for dividing a range (0 to 255) of the value of elasticity of each voxel of the three-dimensional elastic image volume data into plural regions (N: 5 in the present embodiment) and the amount of increase or decrease (01 to 05) in the brightness value in each of the plural divided regions are set in the offset table.

For example, using a graph 181 shown in FIG. 18(*a*), the boundary of regions can be set by moving setting pointers of the boundary values expressed as E0 to E5 left and right through the control panel 26. Similarly, 01 to 05 are pointers indicating the amount of increase or decrease (offset value) in the brightness value of each region, and the offset value of each region can be set by up-and-down movement. The upper and lower limits of the graph 181 are set as 100 and −100, respectively. However, this is just an example, and any values may be set if they are in a range of input and output data. In addition, offset processing is not performed for the input value of elasticity removed from objects to be offset due to the movement of E0 or E5. In addition, E0 and E5 can also be fixed to both ends of the range of the value of elasticity of each voxel. In addition, setting of the boundary value (E0 to E5) or the amount of increase or decrease (01 to 05) in the brightness value can be performed using toggle, an encoder, an adjustment button on a liquid crystal panel, or the like.

In addition, regarding the boundary value and the amount of increase or decrease in the brightness value (offset value), 01 to 05 and E0 to E5 in a display window 182 may also be set by a pull-down menu or direct numeric value input through the control panel 26, as shown in FIG. 18(*b*). In addition, as shown in FIG. 18(*b*), the number of effective regions divided by the boundary values (E0 to E5) may be displayed as the number of brightness adjustment regions 183 (N=5).

Figure 19:
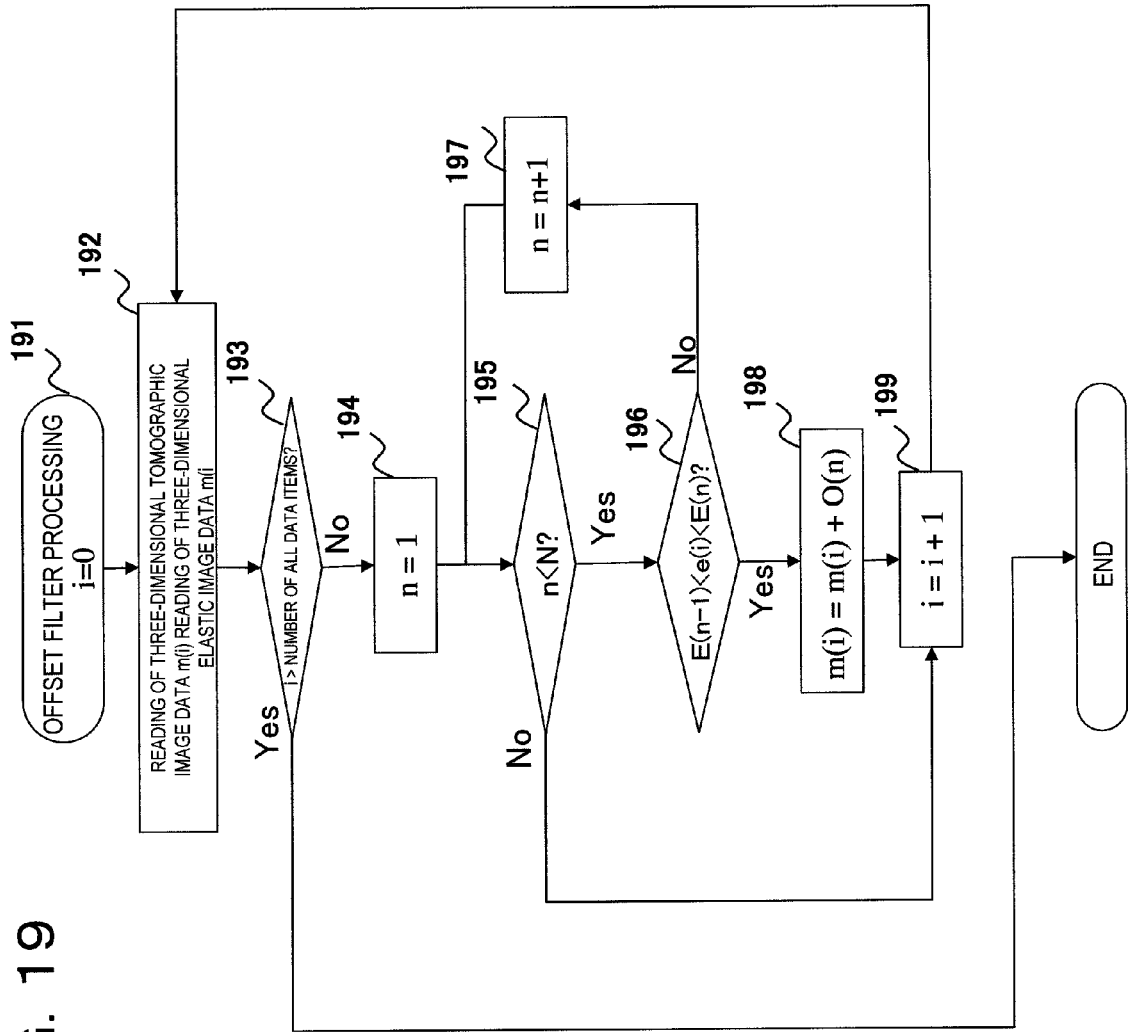
FIG. 19 is a data flow chart of brightness value conversion processing performed by the offset calculating section.

FIG. 19 is a data flow chart of brightness value conversion processing performed by the offset calculating section 16. As shown in FIG. 19, when offset filtering starts in the offset calculating section 16, a counter i is initialized to 0 (step 191). Then, the brightness value m(i) of each voxel of the three-dimensional tomographic image volume data and the value of elasticity e(i) of each voxel of the three-dimensional elastic image volume data are read (step 192). It is determined whether or not i is larger than the total number of data (the number of voxels) (step 193). If i is larger than the total number of data (Yes in step 193), the offset filtering ends. On the other hand, if i is not larger than the total number of data, that is, when offset processing is not performed for all voxels of the three-dimensional tomographic image volume data, the process proceeds to step 194 in which a counter n for region selection is initialized to 1 (step 194).

It is determined whether or not the counter n for region selection is smaller than the number of brightness adjustment regions N (step 195). If the counter n for region selection is smaller than the number of brightness adjustment regions N (Yes in step 195), it is determined whether or not the i-th read value of elasticity e(i) of the three-dimensional elastic image volume data is in a range of E(n−1) to E(n) (step 196). If Yes in step 196, the amount of increase or decrease (offset value) O(n) in the brightness value is added to the brightness value of a corresponding voxel of the three-dimensional tomographic image volume data in step 198 (step 198). On the other hand, if No in step 196, the counter n for region selection is updated and the process returns to step 195 (step 197).

That is, by the loop of steps 195 to 197, the read i-th value of elasticity e(i) of the three-dimensional elastic image volume data is classified into one of the regions divided by the boundary values E(0) to E(N). Then, in step 198, the amount of increase or decrease (offset value) O(n) in the brightness value corresponding to the divided region is added to the brightness value of a corresponding voxel of the three-dimensional tomographic image volume data. After the end of step 198 or if No in step 195, the counter i is updated and the process returns to step 192 (step 199).

Through the above processing, the amount of increase or decrease (offset value) O(n) in the brightness value in each of the regions divided by the boundary values E(0) to E(N) is added to the brightness values of all voxels of the three-dimensional tomographic image volume data. In addition, although the case of performing offset processing using an offset table is shown in the present embodiment, the present invention is not limited to this. For example, it is also possible to set, in the offset calculating section, a function of outputting the amount of increase or decrease in the brightness value of a corresponding voxel of the three-dimensional tomographic image volume data according to the input of the value of elasticity of each voxel of the three-dimensional elastic image volume data and to increase or decrease the brightness value of the corresponding voxel of the three-dimensional tomographic image volume data on the basis of this function.

Similar to the first embodiment, the image combining section 22 displays the two-dimensional tomographic image with the three-dimensional tomographic image on the basis of the output from the tomographic image two-dimensional coordinate transformation section 20 and the output from the tomographic image volume rendering section 18. In addition to this, in the present embodiment, a three-dimensional elastic image obtained by projecting the three-dimensional elastic image volume data onto the two-dimensional projection plane may also be displayed on the image combining section 22 on the basis of the output from the elastic image volume rendering section 176.

According to the present embodiment, an examiner can generate a three-dimensional tomographic image with enhanced visibility of tissue, which has a specific value of elasticity, on the basis of the value of elasticity (stiffness or softness of tissue) of desired specific tissue. For example, if the examiner knows the value of elasticity of desired specific tissue, it is possible to enlarge the amount of increase (offset amount) in the brightness value corresponding to the vicinity of the value of elasticity in advance. On the other hand, when the examiner wants to observe hard (or soft) tissue, a three-dimensional tomographic image of the hard (or soft) tissue with high visibility is displayed if the amount of increase (offset amount) in the brightness value corresponding to the high (or low) value of elasticity is set high. As a result, it becomes easy to observe the hard (or soft) tissue.

(Third Embodiment)

Figure 20:
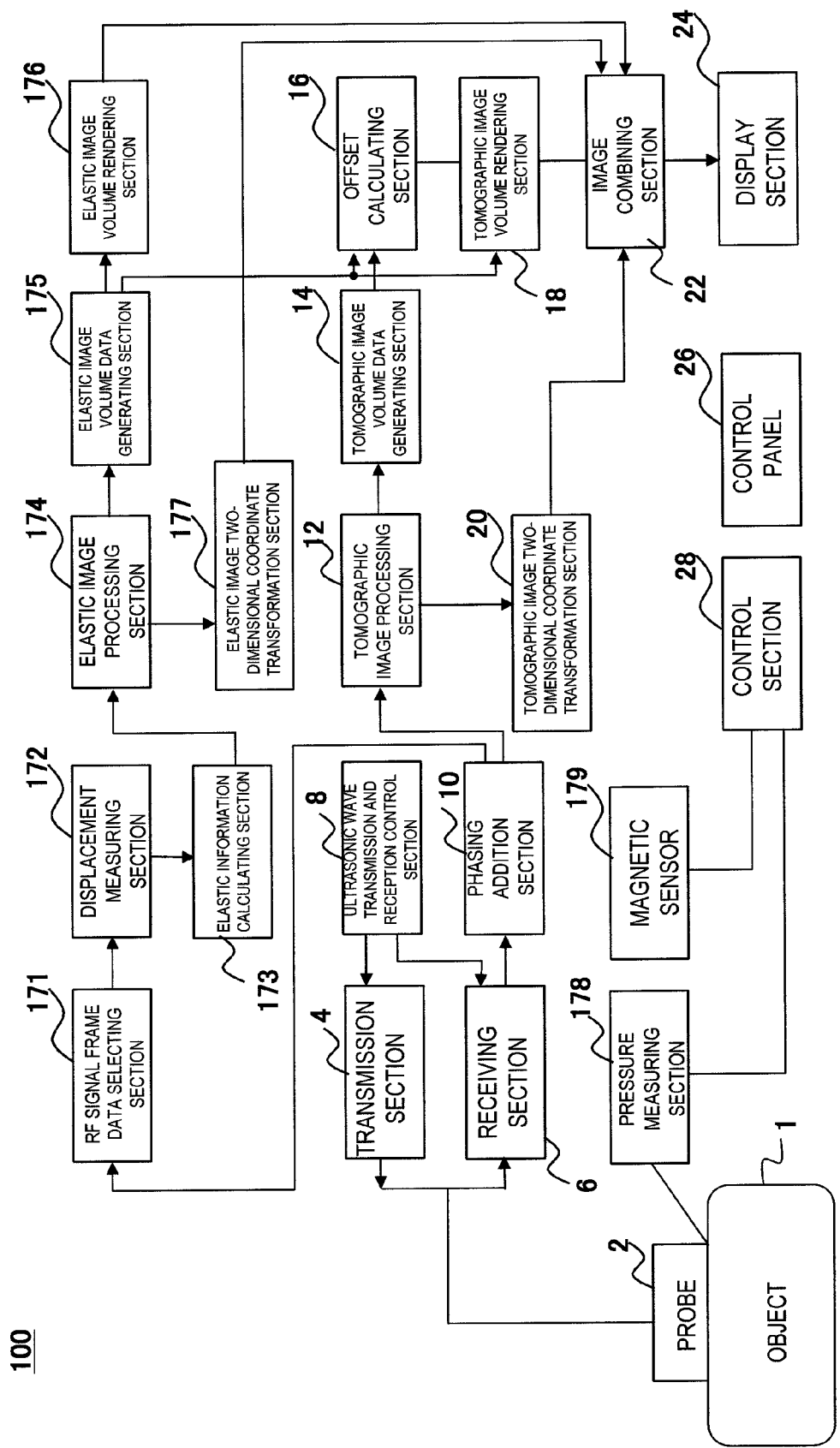
FIG. 20 is a block diagram showing the configuration of an ultrasonic diagnostic apparatus of a third embodiment.

A third embodiment of an ultrasonic diagnostic apparatus to which the present invention is applied will be described with reference to the drawings. FIG. 20 is a block diagram showing the configuration of the ultrasonic diagnostic apparatus of the third embodiment. As shown in FIG. 20, the present embodiment is different from the ultrasonic diagnostic apparatus of the second embodiment in that the output of the elastic image volume data generating section 175 is input to the tomographic image volume rendering section 18 and the tomographic image volume rendering section 18 can refer to the three-dimensional elastic image volume data. Explanation regarding the other same parts as in the second embodiment will be omitted. In the present embodiment, a function of generating a three-dimensional tomographic image that an examiner wants using both the three-dimensional tomographic image volume data and the three-dimensional elastic image volume data is given.

In the present embodiment, the offset calculating section 16 is configured to increase or decrease the brightness value of each voxel according to the brightness value of each voxel of the three-dimensional tomographic image volume data in the same manner as in the first embodiment.

In addition, the control panel 26 has a function of setting the threshold value according to the value of elasticity, and the information regarding the threshold value of the value of elasticity set by the control panel 26 is set in the tomographic image volume rendering section 18 through the control section 28. In the present embodiment, when performing volume rendering of a tomographic image using the above-described Expressions (1) and (2), the tomographic image volume rendering section 18 sets the opacity Ai in Expression (1) to 0 for a corresponding voxel if the value of elasticity of each voxel exceeds (or is less than) the threshold value of the value of elasticity.

Then, brightness conversion of the input brightness value is performed by offset calculation processing. Even if it is opaque, that is, becomes a brightness value to be displayed as a result of comparison using an opacity table, it becomes transparent when the value of elasticity is not present in a target region. As a result, it becomes possible to visualize only the voxel data (brightness data) which is in a range of the target value of elasticity and the target brightness value.

Figure 21:
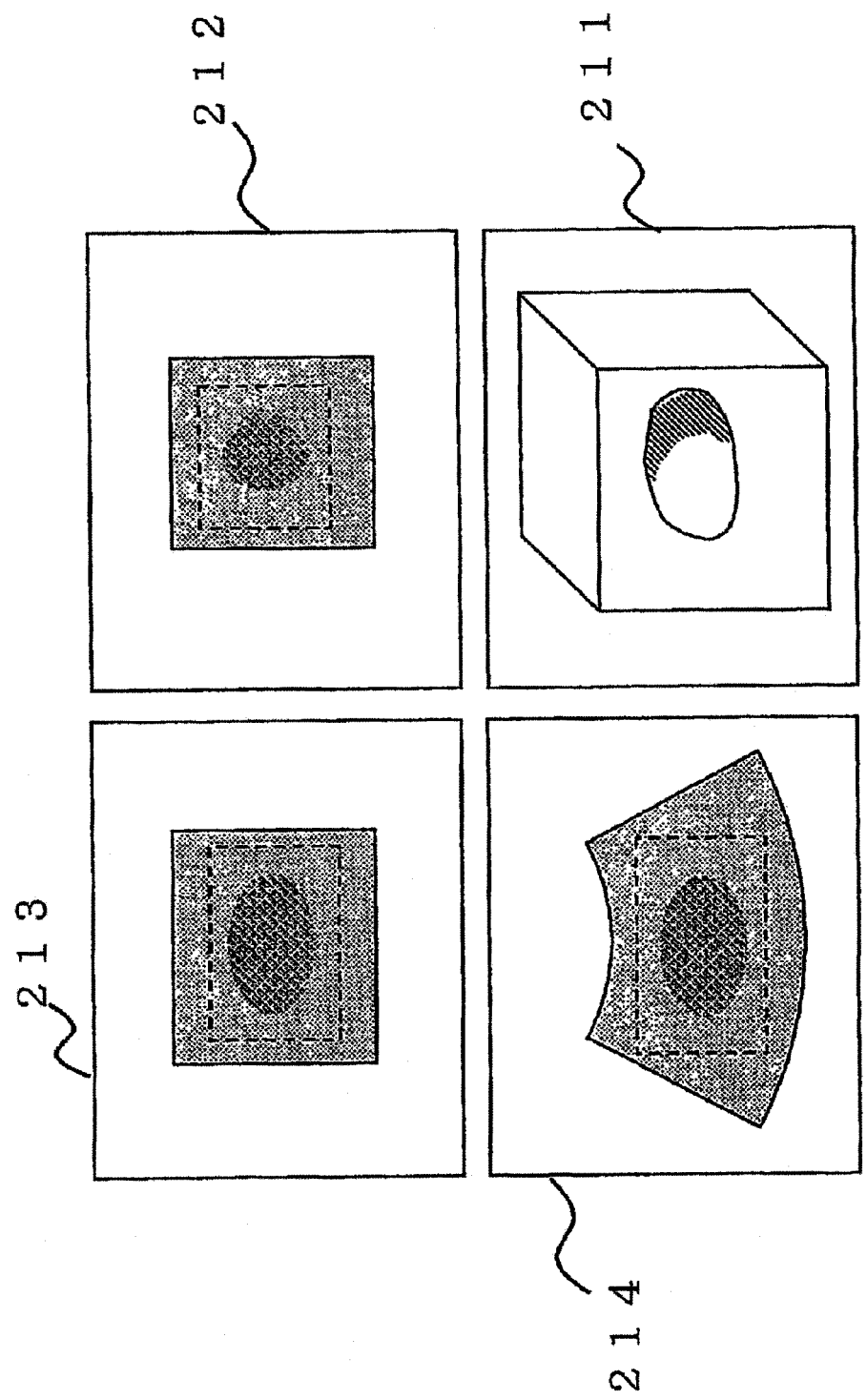
FIG. 21 is a display example when only voxel data (brightness data) which is in a range of the target value of elasticity and the target brightness value is visualized by processing of the third embodiment.

FIG. 21 is a display example when only the voxel data (brightness data) which is in a range of the target value of elasticity and the target brightness value is visualized by processing of the present embodiment. As shown in FIG. 21, it is possible to display a three-dimensional tomographic image 211, in which only the voxel data (brightness data) that is in a range of the target value of elasticity and the target brightness value is visualized, and images 212 and 213, in which a tomographic image and an elastic image on the arbitrary section of the three-dimensional tomographic image 211 overlap each other, side by side.

These images 212 to 214 are generated by the tomographic image two-dimensional coordinate transformation section 20 and the elastic image two-dimensional coordinate transformation section 177 and are overlapped using a method, such as a blending, after color coding processing in the image combining section 22. In addition, as these images 212 and 213, not only three images shown in the drawing but also an arbitrary number of slice images may be simultaneously displayed.

Using the threshold value of the value of elasticity set by the control panel 26, the elastic image volume rendering section 176 can visualize only the surface of an image in the effective display range by setting the value of elasticity of a range, which is to be displayed, to 1.0 and the opacity of a range, which is not to be displayed, to 0.0. In addition, referring to the input brightness of the tomographic image volume data generating section 14, it is possible to visualize only the surface of an image in the effective display range by setting the value of elasticity of a region, in which the opacity of the input brightness is not 0, to 1.0 and the opacity of a range, in which the opacity of the input brightness is 0, to 0.0.

Figure 22:
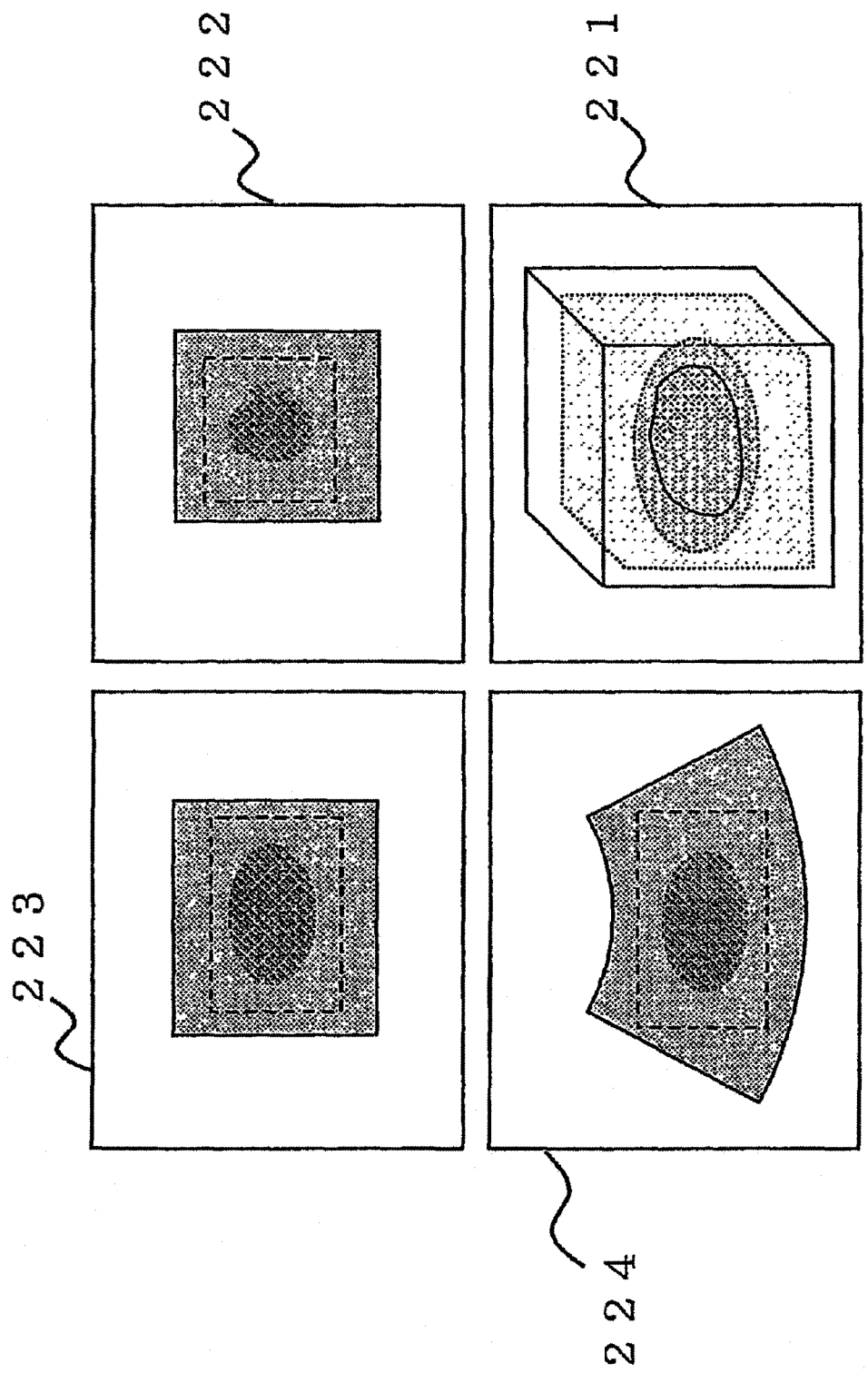
FIG. 22 is a display example when only voxel data (brightness data) which is in a range of the target value of elasticity and the target brightness value is visualized by processing of the third embodiment.

FIG. 22 is a display example when only the voxel data (brightness data) that is in a range of the target value of elasticity and the target brightness value is visualized by processing of the present embodiment. As shown in FIG. 22, it is possible to display a three-dimensional tomographic elastic image 221 and images 222 to 224, in which a tomographic image and an elastic image on the arbitrary section of the three-dimensional tomographic elastic image 221 overlap each other, side by side. The three-dimensional tomographic elastic image 221 is formed by overlapping an image, which is obtained by setting the value of elasticity of the image surface in a three-dimensional manner using the method described above, and an image, which is obtained by setting in a three-dimensional manner the voxel data (brightness data) that is a target value of elasticity and is in a range of a target brightness value, with each other using a method, such as a blending, in the image combining section 22. Compared with the three-dimensional tomographic image 211, it is possible to intuitively distinguish the information regarding the hardness since color display is performed according to the elastic image.

Figure 23:
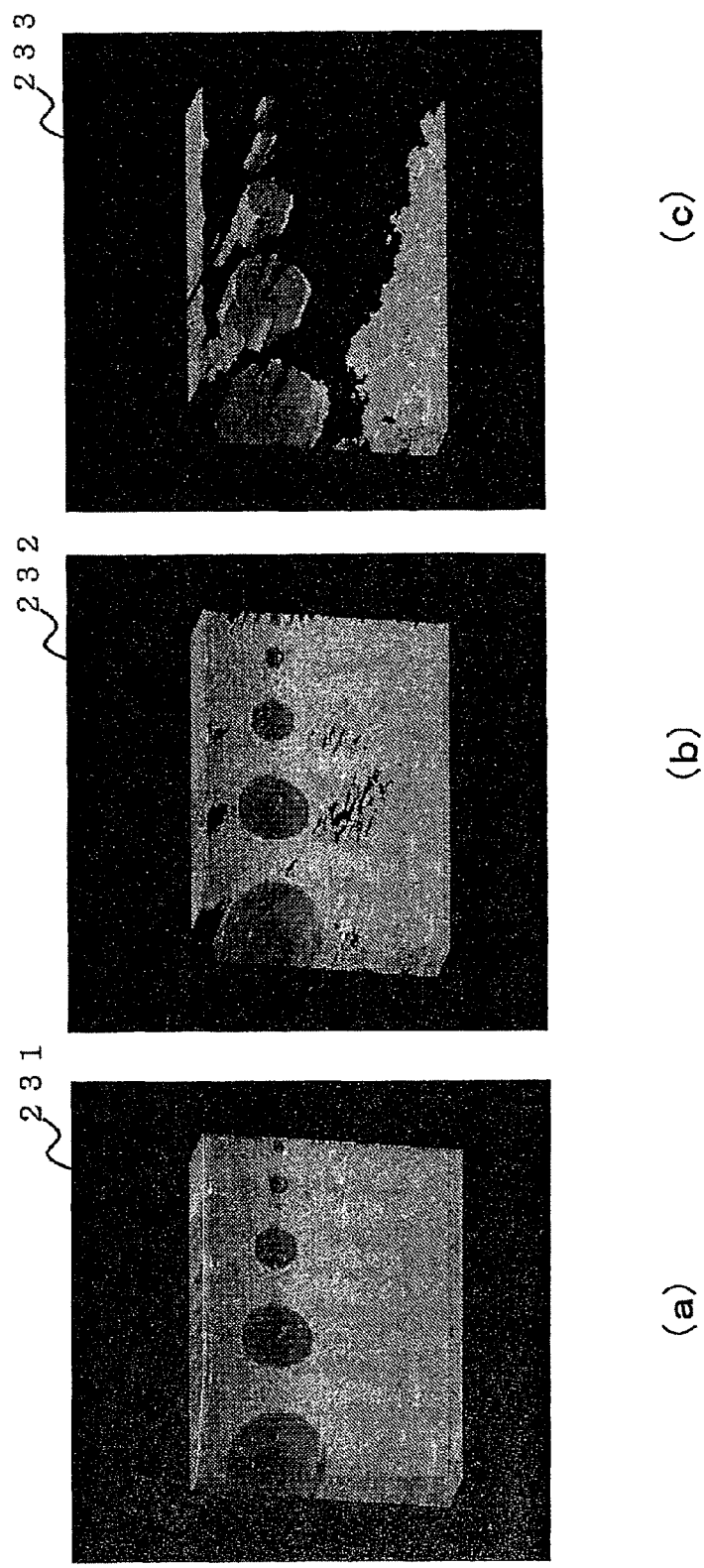
FIG. 23 is a view showing a display example of a three-dimensional tomographic image after performing offset calculation processing using the threshold value according to the value of elasticity.

FIG. 23 is a view showing a display example of a three-dimensional tomographic image using the threshold value according to the value of elasticity described in the above paragraph. At this time, the case in which offset calculation processing is given but setting of an offset filter according to the brightness is not performed is shown in the example. FIGS. 23(*a*), 23(*b*), and 23(*c*) show a three-dimensional tomographic image 231 when there is no threshold value (all displayed), a three-dimensional tomographic image 232 when the threshold value is set to an intermediate value (part of the soft tissue is not displayed), and a three-dimensional tomographic image 233 when the threshold value is set to a high value (only the hard tissue is displayed), respectively.

For example, in the three-dimensional tomographic image 231, it is difficult to observe a depth-direction shape of cylindrical hard tissue, which is formed in a phantom and has low inside brightness. On the other hand, it is possible to gradually make a cylindrical low-brightness region, which is formed in the phantom, easily observable by changing the setting of the threshold value of the value of elasticity as in the three-dimensional tomographic images 232 and 233.

Figure 24:
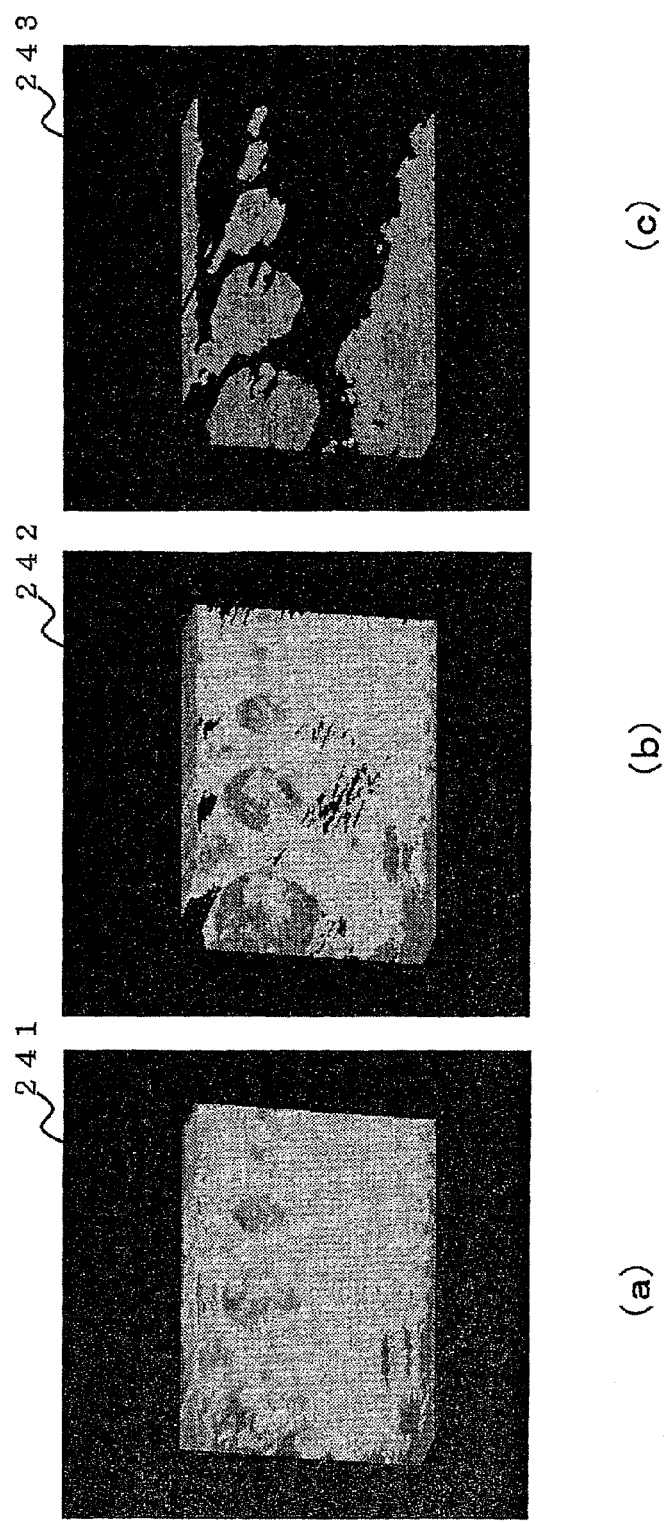
FIG. 24 is a view showing a display example of a three-dimensional elastic image after changing the value of elasticity of a range to be displayed using the threshold value according to the value of elasticity.

FIG. 24 is a view showing a display example of a three-dimensional elastic image after the value of elasticity of a range to be displayed is changed using the threshold value according to the value of elasticity. FIGS. 24(*a*), 24(*b*), and 24(*c*) show a three-dimensional elastic image 241 when there is no threshold value (all displayed), a three-dimensional elastic image 242 when the threshold value is set to an intermediate value (part of the soft tissue is not displayed), and a three-dimensional elastic image 243 when the threshold value is set to a high value (only the hard tissue is displayed), respectively.

Similarly, also in this example, it is difficult to observe a cylindrical low-brightness region formed in a phantom in the three-dimensional elastic image 241. However, it is possible to gradually make the cylindrical low-brightness region, which is formed in the phantom, easily observable by changing the setting of the threshold value of the value of elasticity as in the three-dimensional elastic images 242 and 243.

Figure 25:
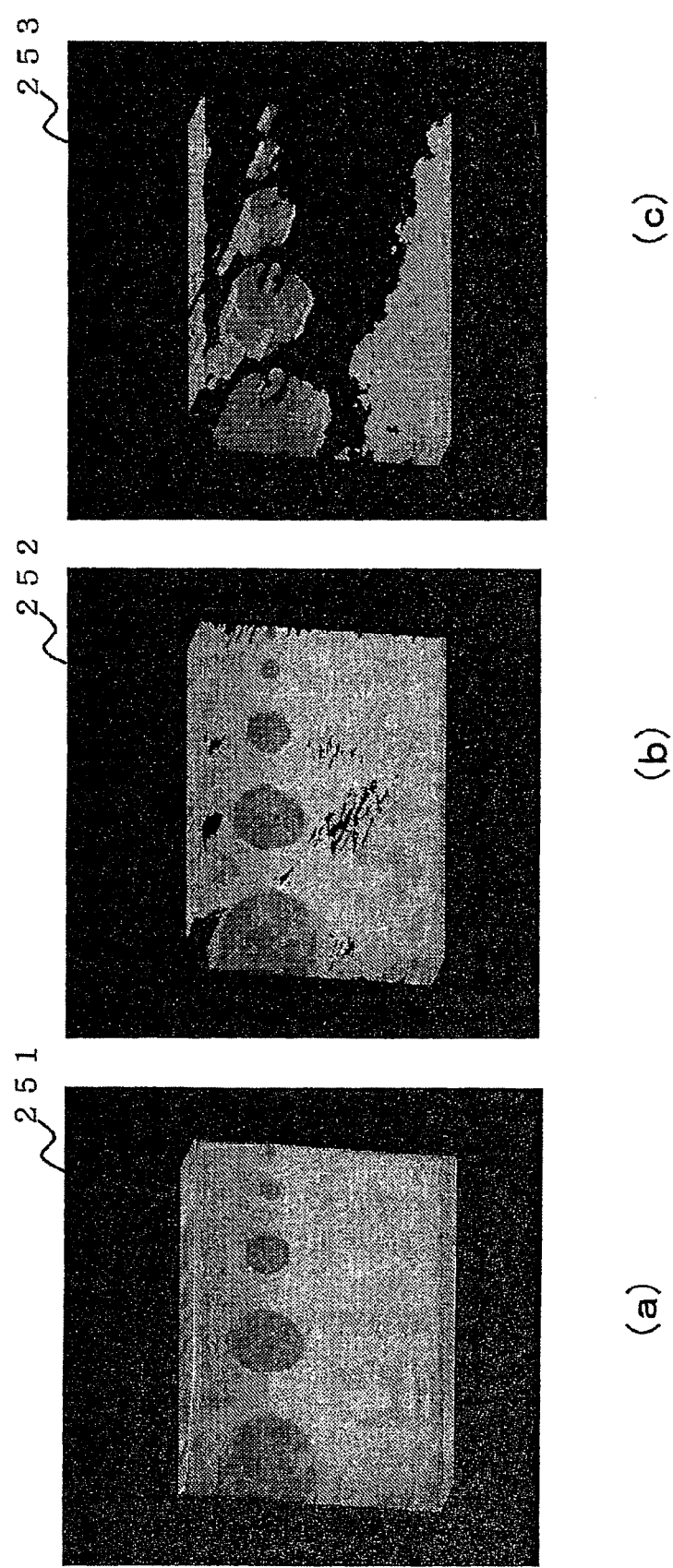
FIG. 25 is an example of an image obtained by overlapping RGB components after RGB conversion of the three-dimensional tomographic image and the three-dimensional elastic image, which are shown in FIGS. 23 and 24, using a blending to add weight.

FIG. 25 is an example of an image obtained by overlapping RGB components after RGB conversion of the three-dimensional tomographic image and the three-dimensional elastic image, which are shown in FIGS. 23 and 24, using a blending to add weight. That is, FIGS. 25(*a*), 25(*b*), and 25(*c*) show a three-dimensional tomographic elastic image 251 when there is no threshold value (all displayed), a three-dimensional tomographic elastic image 252 when the threshold value is set to an intermediate value (part of the soft tissue is not displayed), and a three-dimensional tomographic elastic image 253 when the threshold value is set to a high value (only the hard tissue is displayed), respectively.

Similarly, also in this example, it is difficult to observe a cylindrical low-brightness region formed in a phantom in the three-dimensional tomographic elastic image 251. However, it is possible to gradually make the cylindrical low-brightness region, which is formed in the phantom, easily observable by changing the setting of the threshold value of the value of elasticity as in the three-dimensional tomographic elastic images 252 and 253. In addition, by displaying the three-dimensional tomographic image and the three-dimensional elastic image so as to overlap each other, an image further suitable for diagnosis can be provided to the examiner.

Figure 26:
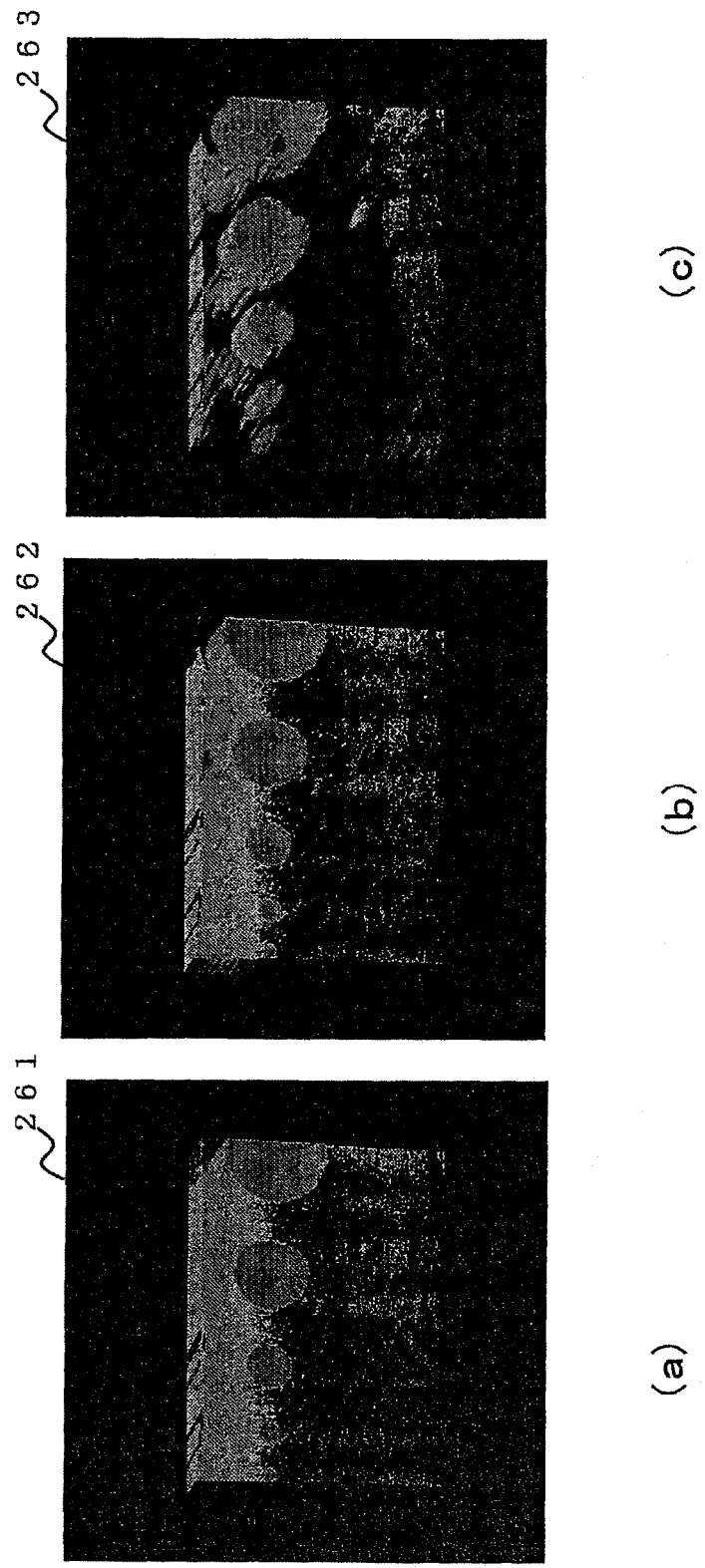
FIG. 26 is a view showing a display example of an image after performing the setting of an offset filter according to the brightness using the threshold value according to the value of elasticity.
Figure 27:
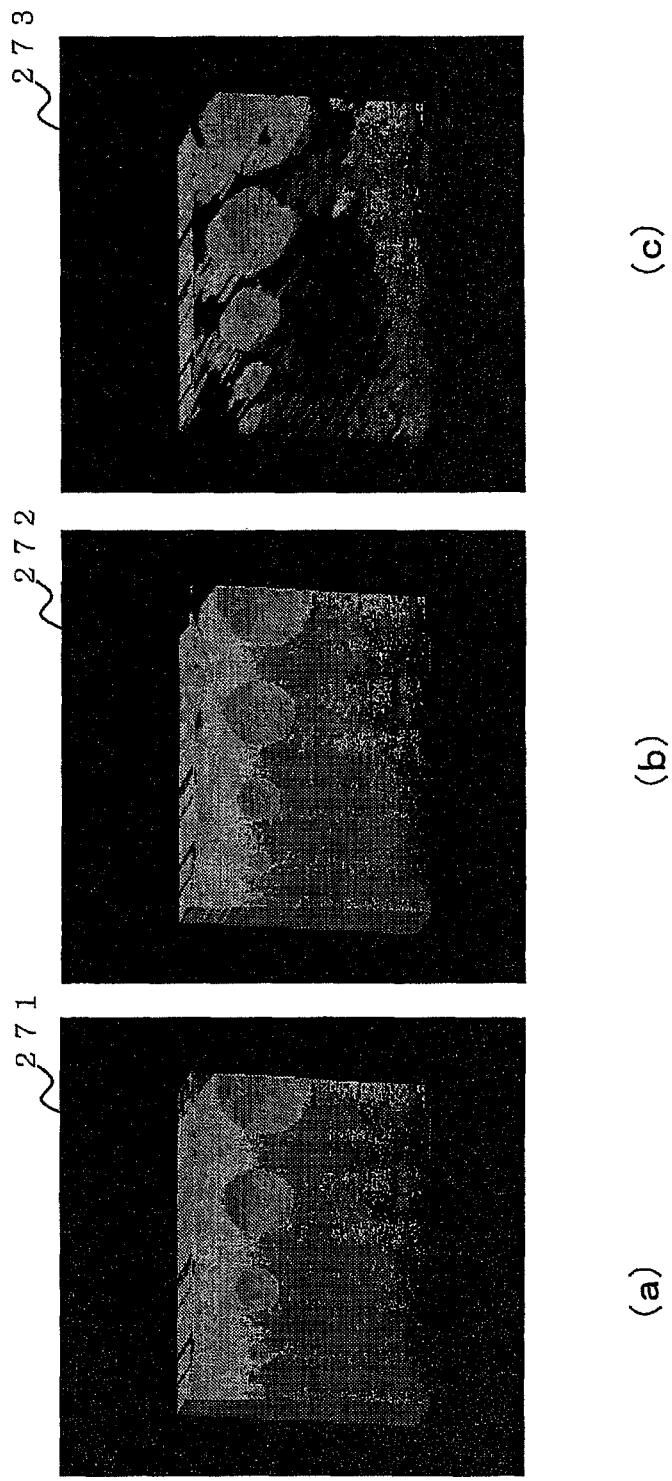
FIG. 27 is a view showing a display example of an image after performing the setting of an offset filter according to the brightness using the threshold value according to the value of elasticity.

Next, FIGS. 26 and 27 show image display examples after performing the setting of an offset filter according to the brightness using the threshold value processing according to the value of elasticity described in the above paragraph. The offset is set so as to emphasize a target observation portion with low brightness and to suppress a portion with brightness equal to or higher than that of the target observation portion.

FIG. 26 shows a display example of a three-dimensional tomographic image after performing the setting of an offset filter according to the brightness using the threshold value according to the value of elasticity described in the above paragraph. FIGS. 26(*a*), 26(*b*), and 26(*c*) show a three-dimensional tomographic image 261 when there is no threshold value (all displayed), a three-dimensional tomographic image 262 when the threshold value is set to an intermediate value (part of the soft tissue is not displayed), and a three-dimensional tomographic image 263 when the threshold value is set to a high value (only the hard tissue is displayed), respectively.

For example, in the three-dimensional tomographic image 261, it is difficult to observe a depth-direction shape of cylindrical hard tissue, which is formed in a phantom and has low inside brightness. On the other hand, it is possible to gradually make a cylindrical low-brightness region, which is formed in the phantom, easily observable by changing the setting of the threshold value of the value of elasticity as in the three-dimensional tomographic images 262 and 263.

FIG. 27 is an example of an image obtained by overlapping RGB components after RGB conversion of the three-dimensional tomographic image and the three-dimensional elastic image after performing the setting of an offset filter according to the brightness using the threshold value according to the value of elasticity, which are shown in FIG. 26, using a blending to add weight. That is, FIGS. 27(*a*), 27(*b*), and 27(*c*) show a three-dimensional elastic image 271 when there is no threshold value (all displayed), a three-dimensional elastic image 272 when the threshold value is set to an intermediate value (part of the soft tissue is not displayed), and a three-dimensional elastic image 273 when the threshold value is set to a high value (only the hard tissue is displayed), respectively.

Similarly, also in this example, it is difficult to observe a cylindrical low-brightness region formed in a phantom in the three-dimensional tomographic elastic image 271. However, it is possible to gradually make the cylindrical low-brightness region, which is formed in the phantom, easily observable by changing the setting of the threshold value of the value of elasticity as in the three-dimensional tomographic elastic images 272 and 273. In addition, by displaying the three-dimensional tomographic image and the three-dimensional elastic image so as to overlap each other, an image further suitable for diagnosis can be provided to the examiner.

In addition, when performing the setting of an offset filter according to the brightness using the threshold value according to the value of elasticity as shown in FIGS. 26 and 27, a low-brightness target observation portion is emphasized by offset processing and displayed with high brightness and a part of a high-brightness peripheral portion is suppressed. On the other hand, the threshold value processing is set so as to display hard tissue and remove soft tissue. Accordingly, a hard target observation portion is displayed and a part of a soft peripheral portion is removed. As a result, since an unnecessary portion which cannot be removed in either the offset processing or the threshold value processing is removed from the three-dimensional image, a target observation portion can be further emphasized and displayed compared with FIGS. 23 and 25.

In addition, although the ultrasonic diagnostic apparatus and the ultrasonic image generation method have been mainly described in the above embodiments, the present invention is not limited to these. For example, the present invention may be applied to an ultrasonic image processing apparatus such as a PC which generates a three-dimensional tomographic image off-line for three-dimensional tomographic image volume data of an object generated in advance by an ultrasonic diagnostic apparatus. In addition, the present invention may also be applied to an ultrasonic image processing program installed in a medical image processing apparatus, such as a PC.

That is, the ultrasonic image processing apparatus, such as a PC, to which the present invention is applied may be configured to include: a memory in which three-dimensional tomographic image volume data generated on the basis of reflected echo signals of plural tomographic planes of an object measured by an ultrasonic probe is stored; a tomographic image volume rendering section which generates a three-dimensional tomographic image seen from at least one line-of-sight direction on the two-dimensional projection plane on the basis of the three-dimensional tomographic image volume data stored in the memory; and a display section which displays the three-dimensional tomographic image.

In addition, the ultrasonic image processing apparatus includes an offset calculating section which increases or decreases the brightness value of each voxel according to the brightness value of each voxel of the three-dimensional tomographic image volume data. The amount of increase or decrease in the brightness value of each voxel of the offset calculating section can be adjusted through an input interface. The tomographic image volume rendering section may be configured to generate a three-dimensional tomographic image on the basis of the three-dimensional tomographic image volume data in which the brightness value has been offset by the offset calculating section.

Moreover, in this ultrasonic image processing apparatus, when the three-dimensional elastic image volume data generated on the basis of the reflected echo signals of the plural tomographic planes of the object is stored in the memory, the offset calculating section may be configured to increase or decrease the brightness value of each corresponding voxel of the three-dimensional tomographic image volume data according to the value of elasticity of each voxel of the three-dimensional elastic image volume data.

An examiner stores the three-dimensional tomographic image volume data of an object generated by an ultrasonic diagnostic apparatus or the like in information recording media, such as a USB and a CD-ROM, to input it to an ultrasonic image processing apparatus, such as a PC, through an image input section, for example. Alternatively, the three-dimensional tomographic image volume data of the object may be input through a network instead of using the information recording media.

Then, the ultrasonic image processing apparatus executes a step of increasing or decreasing the brightness value of each voxel according to the brightness value of each voxel of the three-dimensional tomographic image volume data, a step of generating a three-dimensional tomographic image seen from at least one line-of-sight direction on the two-dimensional projection plane on the basis of the three-dimensional tomographic image volume data in which the brightness value has been offset, and a step of displaying the generated three-dimensional tomographic image as an ultrasonic image processing program.

In addition, when the ultrasonic image processing program includes a step of generating three-dimensional elastic image volume data on the basis of the reflected echo signals of the plural tomographic planes of the object, the brightness value of each corresponding voxel of the three-dimensional tomographic image volume data may be increased or decreased according to the value of elasticity of each voxel of the three-dimensional elastic image volume data in the step of increasing or decreasing the brightness value of each voxel.

According to this, since the examiner can adjust the amount of increase or decrease in the brightness value of each voxel of the offset calculating section off-line through the input interface of the ultrasonic processing apparatus, it is possible to generate a three-dimensional tomographic image in which only tissue with a specific brightness value is emphasized. Therefore, it is possible to generate a three-dimensional tomographic image with enhanced visibility of desired specific tissue by adjusting the amount of increase in the brightness value of the desired specific tissue, adjusting the amount of decrease in the brightness value of tissue other than the desired specific tissue, or adjusting both of them. For example, if the examiner knows the brightness value of desired specific tissue, it is possible to enlarge the amount of increase (offset amount) in the brightness value corresponding to the vicinity of the brightness value in advance. Moreover, for example, in the case where it is difficult to see desired specific tissue since it is hidden behind high-brightness tissue when viewing the generated three-dimensional tomographic image, it becomes difficult for the high-brightness tissue as a wall to be reflected on the three-dimensional tomographic image if the amount of decrease (offset amount) in the brightness value corresponding to the vicinity of the high brightness value is set to be large. As a result, it is possible to improve the visibility of the desired specific tissue.

In addition, since the examiner can adjust the amount of increase or decrease in the brightness value of each voxel of the offset calculating section off-line through the input interface of the ultrasonic processing apparatus on the basis of the value of elasticity (stiffness or softness of tissue) of desired specific tissue, a three-dimensional tomographic image with enhanced visibility of tissue with a specific value of elasticity can be generated. For example, if the examiner knows the value of elasticity of desired specific tissue, it is possible to enlarge the amount of increase (offset amount) in the brightness value corresponding to the vicinity of the value of elasticity in advance. On the other hand, when the examiner wants to observe hard (or soft) tissue, it is possible to find and observe the hard (or soft) tissue if the amount of increase (offset amount) in the brightness value corresponding to the high (or low) value of elasticity is set high.

REFERENCE SIGNS LIST

1: OBJECT
2: ULTRASONIC PROBE
4: TRANSMISSION SECTION
6: RECEIVING SECTION
8: ULTRASONIC WAVE TRANSMISSION AND RECEPTION CONTROL SECTION
10: PHASING ADDITION SECTION
12: TOMOGRAPHIC IMAGE PROCESSING SECTION

14: TOMOGRAPHIC IMAGE VOLUME DATA GENERATING SECTION
16: OFFSET CALCULATING SECTION
18: TOMOGRAPHIC IMAGE VOLUME RENDERING SECTION
20: TOMOGRAPHIC IMAGE TWO-DIMENSIONAL COORDINATE TRANSFORMATION SECTION
22: IMAGE COMBINING SECTION
24: DISPLAY SECTION
26: CONTROL PANEL
28: CONTROL SECTION
111, 123, 135: BRIGHTNESS-OPACITY MAP
171: RF SIGNAL FRAME DATA SELECTING SECTION
172: DISPLACEMENT MEASURING SECTION
173: ELASTIC INFORMATION CALCULATING SECTION
174: ELASTIC IMAGE PROCESSING SECTION
175: ELASTIC IMAGE VOLUME DATA GENERATING SECTION
176: ELASTIC IMAGE VOLUME RENDERING SECTION
177: ELASTIC IMAGE TWO-DIMENSIONAL COORDINATE TRANSFORMATION SECTION

The invention claimed is:

1. An ultrasonic diagnostic apparatus comprising:
an ultrasonic probe which transmits or receives an ultrasonic wave to or from an object;
a tomographic image volume data generating section which generates three-dimensional tomographic image volume data based on reflected echo signals of a plurality of tomographic planes of the object measured by the ultrasonic probe;
a tomographic image volume rendering section which generates a three-dimensional tomographic image from at least one line-of-sight direction on a two-dimensional projection plane based on the three-dimensional tomographic image volume data;
a display section which displays the three-dimensional tomographic image; and
an offset calculating section which increases or decreases a brightness value of each voxel of the three-dimensional tomographic image volume data based on the brightness value of each voxel,
wherein the offset calculating section divides a range of the brightness value of each voxel of the three-dimensional tomographic image data into a plurality of regions, and an amount of increase or decrease in each of the plurality of regions is set,
wherein an amount of increase or decrease in the brightness value of each voxel is based on the amount increase or decrease set in each of the plurality of regions, and the amount of increase or decrease in the brightness value of each voxel is adjustable via an input interface, and
wherein the tomographic image volume rendering section generates the three-dimensional tomographic image based on the three-dimensional tomographic image volume data in which the brightness value is offset by the offset calculating section.

2. The ultrasonic diagnostic apparatus according to claim 1, further comprising:
an elastic image volume data generating section which generates three-dimensional elastic image volume data based on the reflected echo signals of the plurality of tomographic planes of the object,
wherein the offset calculating section increases or decreases the brightness value of each corresponding voxel of the three-dimensional tomographic image volume data based on the value of elasticity of each voxel of the three-dimensional elastic image volume data.

3. The ultrasonic diagnostic apparatus according to claim 1,
wherein the offset calculating section has a plurality of offset tables in which boundary values for dividing the range of the brightness value of each voxel of the three-dimensional tomographic image volume data into the plurality of regions and the amount of increase or decrease in the brightness value in each of the plurality of divided regions are set, and
wherein the brightness value of each voxel of the three-dimensional tomographic image volume data is increased or decreased based on the offset table selected from the plurality of offset tables via the input interface.

4. The ultrasonic diagnostic apparatus according to claim 3,
wherein the boundary value and the amount of increase or decrease of the offset table are adjustable via the input interface.

5. The ultrasonic diagnostic apparatus according to claim 1,
wherein the tomographic image volume rendering section has an opacity table in which transparency/opacity is set according to the brightness value of each voxel of the three-dimensional tomographic image volume data, and
wherein the three-dimensional tomographic image is generated based on the brightness value of each voxel on a line of sight in the at least one line-of-sight direction of the three-dimensional tomographic image volume data and the transparency/opacity based on the opacity table.

6. The ultrasonic diagnostic apparatus according to claim 1,
wherein the tomographic image volume rendering section has a brightness-opacity map in which transparency/opacity and a color code are set according to the brightness value of each voxel of the three-dimensional tomographic image volume data and includes means for generating a two-dimensional tomographic image by converting a color of each voxel of tomographic image data of at least one section of the three-dimensional tomographic image volume data, in which the brightness value is offset, based on the brightness-opacity map, and
wherein the display section displays the three-dimensional tomographic image, the two-dimensional tomographic image, and the brightness-opacity map.

7. The ultrasonic diagnostic apparatus according to claim 2,
wherein the offset calculating section increases or decreases the brightness value of each voxel according to the brightness value of each voxel of the three-dimensional tomographic image volume data,
wherein the tomographic image volume rendering section increases or decreases the transparency/opacity of each voxel according to the value of elasticity of each voxel of the three-dimensional elastic image volume data, and generates the three-dimensional tomographic image based on the increased or decreased brightness value of each voxel of the three-dimensional tomographic image volume data and the increased or decreased transparency/opacity.

8. The ultrasonic diagnostic apparatus according to claim 2, further comprising:
an elastic image volume rendering section which generates a three-dimensional elastic image seen from at least one line-of-sight direction on the two-dimensional projection plane based on the three-dimensional elastic image volume data; and an image combining section which generates a three-dimensional tomographic elastic image by overlapping the three-dimensional tomographic image generated by the tomographic image volume rendering section and the three-dimensional elastic image generated by the elastic image volume rendering section with each other, wherein the display section displays the three-dimensional tomographic elastic image.

9. A computer program product for processing an ultrasonic image, the computer program product comprising:

a computer program; and a non-transitory computer-readable storage medium having the computer program tangibly embodied thereon, wherein the computer program causes the computer to perform;

a step of generating a three-dimensional tomographic image from at least one line-of-sight direction on a two-dimensional projection plane based on three-dimensional tomographic image volume data generated based on reflected echo signals of a plurality of tomographic planes of an object measured by an ultrasonic probe;

a step of displaying the three-dimensional tomographic image; and a step of increasing or decreasing the brightness value of each voxel of the three-dimensional tomographic image volume data based on the brightness value of each voxel:

a step of dividing a range of the brightness value of each voxel of the three-dimensional tomographic image data into a plurality of regions, and setting an amount of increase or decrease in each of plurality of regions, wherein an of increase or decrease in the brightness value of each voxel is based on the amount of increase or decrease set in each of the plurality of regions, and the amount of increase or decrease in the brightness value of each voxel in the step of increasing or decreasing the brightness value of each voxel is adjustable via an input interface, and wherein in the step of generating the three-dimensional tomographic image, the three-dimensional tomographic image is generated based on the three-dimensional tomographic image volume data in which the brightness value is offset.

10. The computer program product according to claim 9, wherein the computer program further causes the computer to perform:

a step of generating three-dimensional elastic image volume data based on the reflected echo signals of the plurality of tomographic planes of the object, wherein in the step of increasing or decreasing the brightness value of each voxel, the brightness value of each corresponding voxel of the three-dimensional tomographic image volume data is increased or decreased according to the value of elasticity of each voxel of the three-dimensional elastic image volume data.

11. An ultrasonic image generation method comprising:

a step of generating a three-dimensional tomographic image from at least one line-of-sight direction on a two-dimensional projection plane based on three-dimensional tomographic image volume data generated based on reflected echo signals of a plurality of tomographic planes of an object measured by an ultrasonic probe;

a step of displaying the three-dimensional tomographic image; and a step of increasing or decreasing a brightness value of each voxel of the three-dimensional tomographic image volume data based on the brightness value of each voxel;

a step of dividing a range of the brightness value of each voxel of the three-dimensional tomographic image data into a plurality of regions, and setting an amount of increase or decrease in each of the plurality of regions, wherein an amount of increase or decrease in the brightness value of each voxel is based on the amount of increase or decrease set in each of the plurality of regions, and the amount of increase or decrease in the brightness value of each voxel in the step of increasing or decreasing the brightness value of each voxel is adjustable via an input interface, and wherein, in the step of generating the three-dimensional tomographic image, the three-dimensional tomographic image is generated based on the three-dimensional tomographic image volume data in which the brightness value is offset.

12. The ultrasonic image generation method according to claim 11, further comprising:

a step of generating three-dimensional elastic image volume data based on the reflected echo signals of the plurality of tomographic planes of the object, wherein in the step of increasing or decreasing the brightness value of each voxel, the brightness value of each corresponding voxel of the three-dimensional tomographic image volume data is increased or decreased according to the value of elasticity of each voxel of the three-dimensional elastic image volume data.

13. The ultrasonic diagnostic apparatus according to claim 2, wherein the offset calculating section has a plurality of offset tables in which boundary values for dividing a range of the value of elasticity of each voxel of the three-dimensional elastic image volume data into a plurality of regions and the amount of increase or decrease in the brightness value in each of the plurality of divided regions are set, and wherein the brightness value of each voxel of the three-dimensional tomographic image volume data is increased or decreased based on the offset table selected from the plurality of offset tables via the input interface.

* * * * *